(12) United States Patent
Thorgilsdottir et al.

(10) Patent No.: US 8,038,636 B2
(45) Date of Patent: Oct. 18, 2011

(54) CERVICAL COLLAR HAVING HEIGHT AND CIRCUMFERENTIAL ADJUSTMENT

(75) Inventors: Thora Thorgilsdottir, Reykjavik (IS); Arni Thor Ingimundarson, Ladera Ranch, CA (US); Palmi Einarsson, San Juan Capistrano, CA (US)

(73) Assignee: Ossur HF, Reykjavik (IS)

( * ) Notice: Subject to any disclaimer, the term of this patent is extended or adjusted under 35 U.S.C. 154(b) by 0 days.

(21) Appl. No.: 13/114,439

(22) Filed: May 24, 2011

(65) Prior Publication Data
US 2011/0224591 A1 Sep. 15, 2011

Related U.S. Application Data

(63) Continuation of application No. 12/629,197, filed on Dec. 2, 2009, now Pat. No. 7,981,068.

(60) Provisional application No. 61/119,425, filed on Dec. 3, 2008, provisional application No. 61/241,528, filed on Sep. 11, 2009.

(51) Int. Cl.
*A61F 5/00* (2006.01)
*A61F 5/37* (2006.01)
(52) U.S. Cl. ............... 602/18; 602/5; 602/19; 128/846
(58) Field of Classification Search ............. 602/18, 602/19, 17, 5; 128/846, DIG. 23
See application file for complete search history.

(56) References Cited

U.S. PATENT DOCUMENTS

| | | |
|---|---|---|
| 2,818,063 A | 12/1957 | Smith et al. |
| 2,911,970 A | 11/1959 | Bartels et al. |
| 3,024,784 A | 3/1962 | Monfardini |
| 3,042,027 A | 7/1962 | Monfardini |
| 3,306,284 A | 2/1967 | McKinley |
| 3,504,667 A | 4/1970 | McFarlane |
| 3,512,523 A | 5/1970 | Barnett |
| 3,756,226 A | 9/1973 | Calabrese et al. |
| 3,916,885 A | 11/1975 | Gaylord, Jr. |
| 4,205,667 A | 6/1980 | Gaylord, Jr. |
| 4,401,111 A | 8/1983 | Blackstone |
| 4,413,619 A | 11/1983 | Garth |
| 4,538,597 A | 9/1985 | Lerman |
| 4,712,540 A | 12/1987 | Tucker et al. |
| 4,745,922 A | 5/1988 | Taylor |
| 4,886,052 A | 12/1989 | Calabrese |
| 4,940,043 A | 7/1990 | Burns et al. |

(Continued)

FOREIGN PATENT DOCUMENTS

WO 95/22304 A1 8/1995

OTHER PUBLICATIONS

International Search Report issued in PCT/US2009/006335, Mar. 11, 2010, 3 pages.

(Continued)

*Primary Examiner* — Michael Brown
*Assistant Examiner* — Ophelia Hawthorne
(74) *Attorney, Agent, or Firm* — Bacon & Thomas, PLLC

(57) ABSTRACT

An orthopedic device in the form of a cervical collar having height and circumferential adjustment includes an anterior portion and a posterior portion. The anterior portion includes a main support piece having depending projections configured to engage a height adjustment mechanism. Each of the anterior and posterior portions also includes a proximal support portion having a three-dimensional anatomically configured shape to support, immobilize, and stabilize an anatomical portion of a wearer. The anterior and/or posterior portion includes circumferential adjustment mechanisms to accommodate different sizes or differing degrees of swelling of anatomical portions.

20 Claims, 18 Drawing Sheets

U.S. PATENT DOCUMENTS

| | | |
|---|---|---|
| 5,005,563 A | 4/1991 | Veale |
| 5,038,759 A | 8/1991 | Morgenstern |
| 5,058,572 A | 10/1991 | Schmid et al. |
| 5,097,824 A | 3/1992 | Garth |
| 5,156,588 A | 10/1992 | Marcune et al. |
| 5,180,361 A | 1/1993 | Moore et al. |
| 5,215,517 A | 6/1993 | Stevenson et al. |
| 5,230,698 A | 7/1993 | Garth |
| 5,275,581 A | 1/1994 | Bender |
| 5,302,170 A | 4/1994 | Tweardy |
| RE34,714 E | 8/1994 | Burns et al. |
| 5,366,438 A | 11/1994 | Martin, Sr. |
| 5,385,535 A | 1/1995 | McGuinness |
| 5,433,696 A | 7/1995 | Osti |
| 5,437,612 A | 8/1995 | Moore et al. |
| 5,445,602 A | 8/1995 | Grim et al. |
| D368,527 S | 4/1996 | Brooke |
| D369,660 S | 5/1996 | Myoga |
| 5,520,619 A | 5/1996 | Martin |
| RE35,290 E | 7/1996 | Druskoczi |
| 5,588,957 A | 12/1996 | Martin, Sr. |
| 5,593,382 A | 1/1997 | Rudy, Jr. et al. |
| 5,622,529 A | 4/1997 | Calabrese |
| 5,624,387 A | 4/1997 | McGuinness |
| D379,232 S | 5/1997 | Brooke |
| 5,632,722 A | 5/1997 | Tweardy et al. |
| 5,688,229 A | 11/1997 | Bauer |
| 5,716,335 A | 2/1998 | Iglesias et al. |
| 5,728,054 A | 3/1998 | Martin |
| D393,718 S | 4/1998 | Traut et al. |
| 5,785,670 A | 7/1998 | Hiebert |
| 5,788,658 A | 8/1998 | Islava |
| 5,795,315 A | 8/1998 | Traut et al. |
| 5,797,713 A | 8/1998 | Tweardy et al. |
| 5,797,863 A | 8/1998 | Kohnke |
| 5,865,773 A | 2/1999 | Koledin |
| 5,904,662 A | 5/1999 | Myoga |
| 5,964,722 A | 10/1999 | Goralnik et al. |
| 5,976,098 A | 11/1999 | Sereboff |
| 5,993,403 A | 11/1999 | Martin |
| 6,027,467 A | 2/2000 | Nakamura et al. |
| 6,036,664 A | 3/2000 | Martin, Sr. et al. |
| D422,710 S | 4/2000 | Maynard |
| 6,045,523 A | 4/2000 | Donaldson |
| 6,050,965 A | 4/2000 | Pillai |
| 6,056,711 A | 5/2000 | Donamski et al. |
| 6,058,517 A | 5/2000 | Hartunian |
| RE36,745 E | 6/2000 | Rudy, Jr. et al. |
| 6,071,255 A | 6/2000 | Calabrese |
| 6,071,256 A | 6/2000 | Lam |
| 6,090,058 A | 7/2000 | Traut et al. |
| 6,165,146 A | 12/2000 | Giebeler |
| 6,183,501 B1 | 2/2001 | Latham |
| 6,245,033 B1 | 6/2001 | Martin |
| 6,254,560 B1 | 7/2001 | Tweardy et al. |
| 6,308,345 B1 | 10/2001 | Williams, Jr. |
| 6,423,020 B1 | 7/2002 | Koledin |
| 6,458,090 B1 | 10/2002 | Walpin |
| 6,494,854 B1 | 12/2002 | Visness et al. |
| D475,139 S | 5/2003 | Myoga |
| 6,663,581 B1 | 12/2003 | Calabrese |
| 6,663,630 B2 | 12/2003 | Farley et al. |
| 6,726,643 B1 | 4/2004 | Martin |
| 6,740,055 B2 | 5/2004 | Dominguez |
| 6,770,046 B2 | 8/2004 | Hansen |
| 6,872,188 B2 | 3/2005 | Caille et al. |
| 6,913,584 B2 | 7/2005 | Rudy, Jr. et al. |
| 6,921,376 B2 | 7/2005 | Tweardy et al. |
| 6,926,686 B2 | 8/2005 | Cheatham |
| 7,018,351 B1 | 3/2006 | Iglesias et al. |
| 7,041,073 B1 | 5/2006 | Patron |
| 7,070,573 B2 | 7/2006 | Axelsson |
| 7,090,652 B2 | 8/2006 | Santelli, Jr. |
| 7,090,653 B2 | 8/2006 | Moeller |
| 7,128,724 B2 | 10/2006 | Marsh |
| 7,141,031 B2 | 11/2006 | Garth et al. |
| 7,198,610 B2 | 4/2007 | Ingimundarson et al. |
| D542,919 S | 5/2007 | Leatt |
| 7,258,677 B2 | 8/2007 | Rudy, Jr. et al. |
| 7,291,121 B2 | 11/2007 | Rudy, Jr. et al. |
| 7,297,127 B2 | 11/2007 | Lee et al. |
| 7,311,686 B1 | 12/2007 | Iglesias et al. |
| 7,371,221 B1 | 5/2008 | Baker |
| 7,371,222 B2 | 5/2008 | Heinz et al. |
| 7,399,288 B2 | 7/2008 | Chao |
| 2002/0138028 A1 | 9/2002 | Rudy, Jr. et al. |
| 2002/0156408 A1 | 10/2002 | Cheatham |
| 2002/0156409 A1 | 10/2002 | Lee et al. |
| 2002/0169401 A1 | 11/2002 | Walpin |
| 2002/0173737 A1 | 11/2002 | Miyaji et al. |
| 2003/0055367 A1 | 3/2003 | Dominguez |
| 2003/0060744 A1 | 3/2003 | Caille et al. |
| 2003/0181838 A1 | 9/2003 | Garth |
| 2004/0039318 A1 | 2/2004 | Santelli, Jr. |
| 2005/0101896 A1 | 5/2005 | Calabrese |
| 2007/0027418 A1 | 2/2007 | Calco et al. |
| 2007/0270728 A1 | 11/2007 | Chao |

OTHER PUBLICATIONS

Written Opinion of the International Searching Authority issued in PCT/US2009/006335, Mar. 11, 2010, 5 pages.

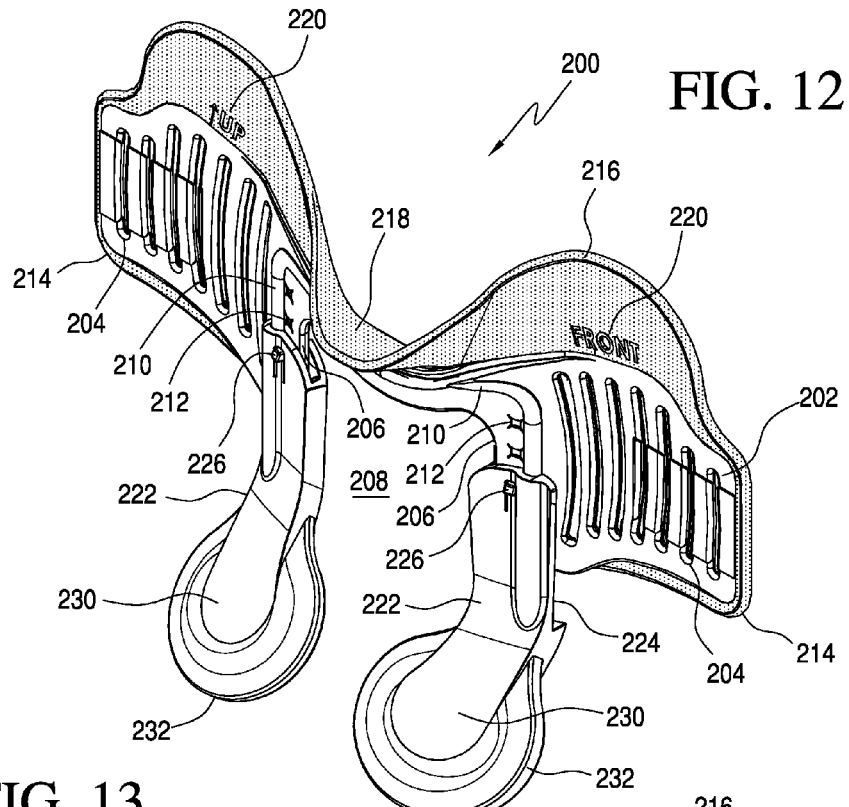
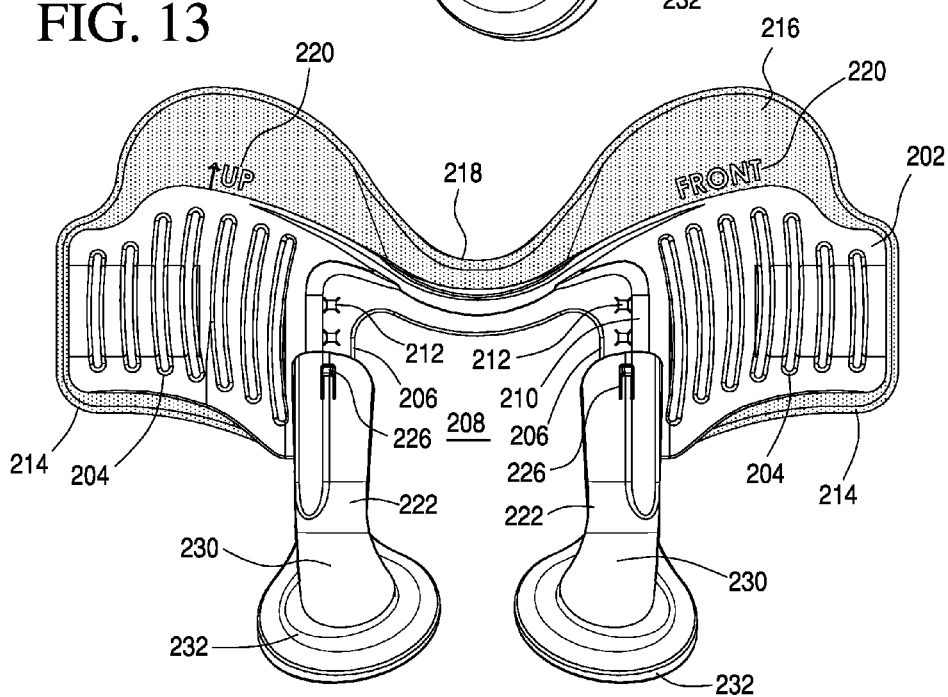

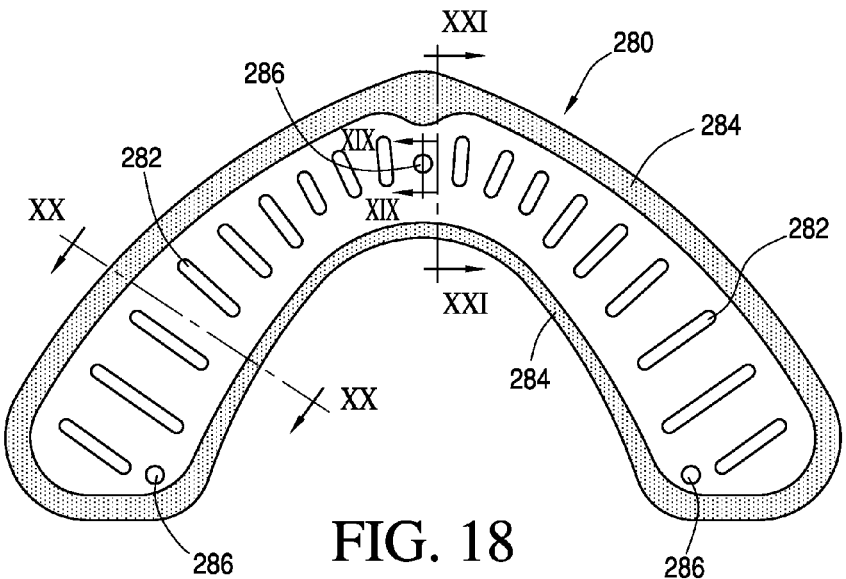
FIG. 18
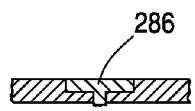
FIG. 19
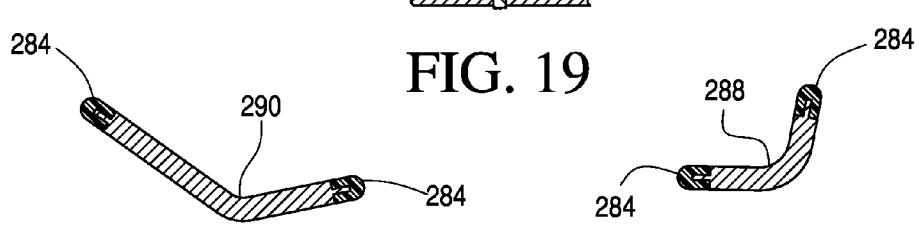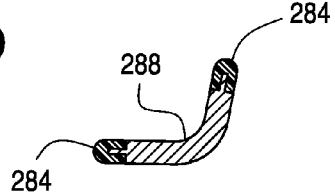
FIG. 20  FIG. 21
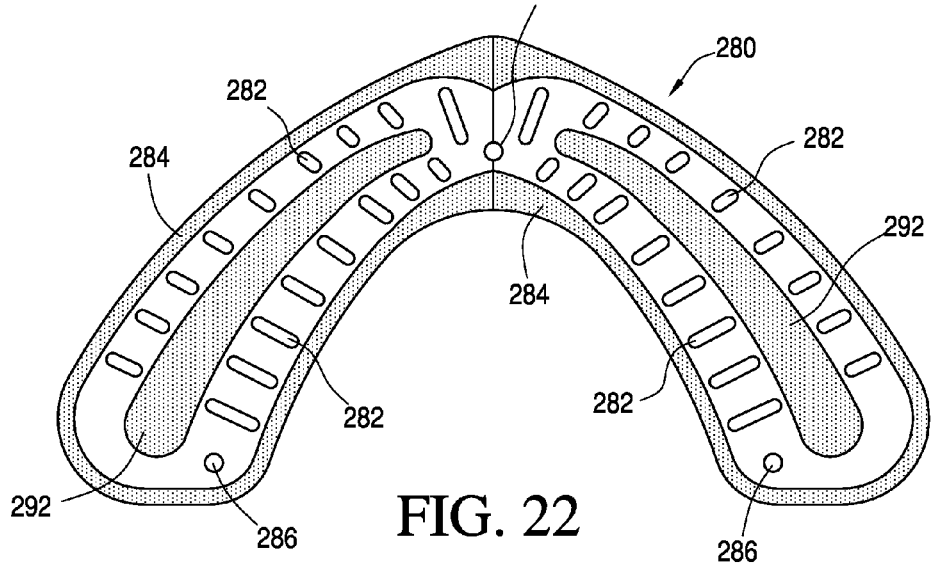
FIG. 22

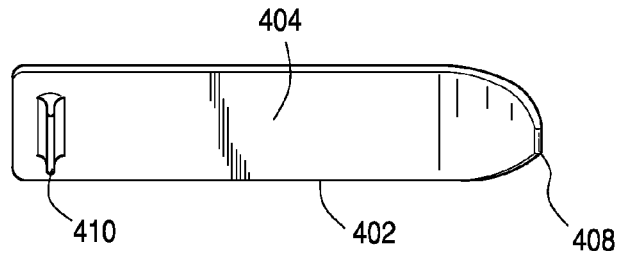
FIG. 38
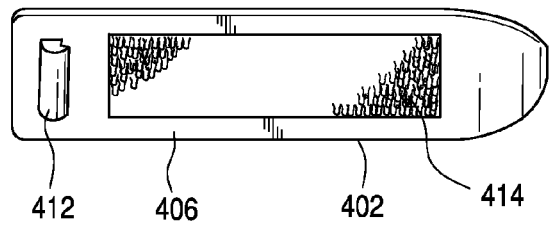
FIG. 39
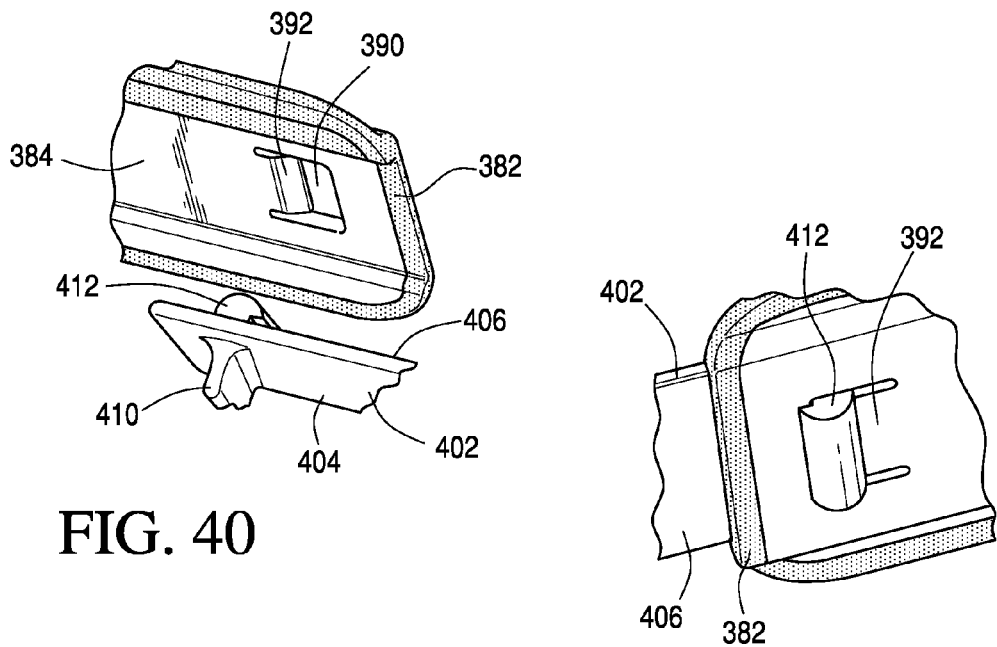
FIG. 40
FIG. 41

CERVICAL COLLAR HAVING HEIGHT AND CIRCUMFERENTIAL ADJUSTMENT

This application is a continuation of U.S. application Ser. No. 12/629,197 which claims the benefit of priority from U.S. Provisional Application No. 61/119,425, filed Dec. 3, 2008, and U.S. Provisional Application No. 61/241,528, filed Sep. 11, 2009.

FIELD OF THE INVENTION

The invention relates generally to the field of orthopedic or prosthetic devices and more specifically to cervical collars having height and circumferential adjustment

BACKGROUND

Cervical collars are used in the treatment, stabilization, immobilization, and therapy of cervical trauma. For example, some collars are intended to provide support for whiplash and other such injuries where support for the head and neck is needed. Other collars are intended for near complete immobilization of the head and neck, such as in an EMS pre-hospital setting.

SUMMARY

The present invention provides a cervical collar having height and circumferential adjustment in order to accommodate a wide variety of sizes of different patients and to accommodate size changes caused by increased or decreased swelling of the affected anatomical portions of the patients.

Additional features of the cervical collar include a removable adjustable height support piece to allow the collar to be adjusted or removed, for example for cleaning or to check for pressure sores, without removing life support attachments such as breathing and feeding tubes.

Flexible or compliant edges and anatomically shaped portions on the cervical collar are provided to accommodate different sized users, to accommodate changes in anatomical shape due to an increase or decrease in swelling, and to prevent pressure peaks, even if the collar is improperly applied to the patient.

The disclosed cervical collar is configured to conform to the anatomy of the patient, and to further to be a generally constant contact collar that contacts the skin of the patient such that when the collar does allow some amount of patient movement, the collar moves with the patient.

The combination of flexible or compliant edges and anatomically shaped portions on the cervical collar along with ventilation mechanisms, such as ventilation slots, allow the collar to have intimate contact with the skin of the patient (with or without the use of a liner).

BRIEF DESCRIPTION OF THE DRAWINGS

These and other features, aspects, and advantages of the present invention will become better understood with regard to the following description, appended claims, and accompanying drawings where:

FIG. 12 is a perspective view of a another configuration of an anterior portion of a cervical collar in accordance with the present disclosure;

FIG. 13 is a front view of the anterior portion of the cervical collar shown in FIG. 12;

FIG. 18 is a top view of a variation of a chin support piece in accordance with the present disclosure;

FIG. 19 is a sectional view taken along line XIX-XIX in FIG. 18;

FIG. 20 is a sectional view taken along line XX-XX in FIG. 18;

FIG. 21 is a sectional view taken along line XXI-XXI in FIG. 18;

FIG. 22 is a top view of a further variation of a chin support piece in accordance with the present disclosure;

FIG. 38 is a front view of a side connection piece for use with the posterior portion of the cervical collar shown in FIG. 36;

FIG. 39 is a rear view of the side connection piece shown in FIG. 38;

FIGS. 40 and 41 are expanded partial views of the connection between the posterior portion of the cervical collar shown in FIG. 36 and the side connection piece shown in FIG. 36;

Figure 1:
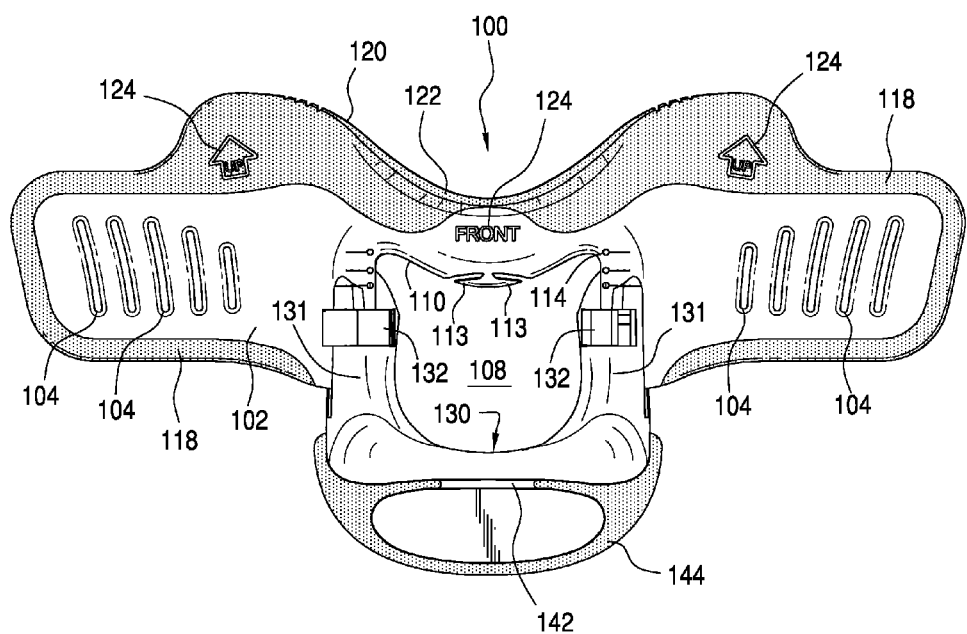
FIG. 1 is a front view of an anterior portion of a cervical collar in accordance with the present disclosure.
Figure 2:
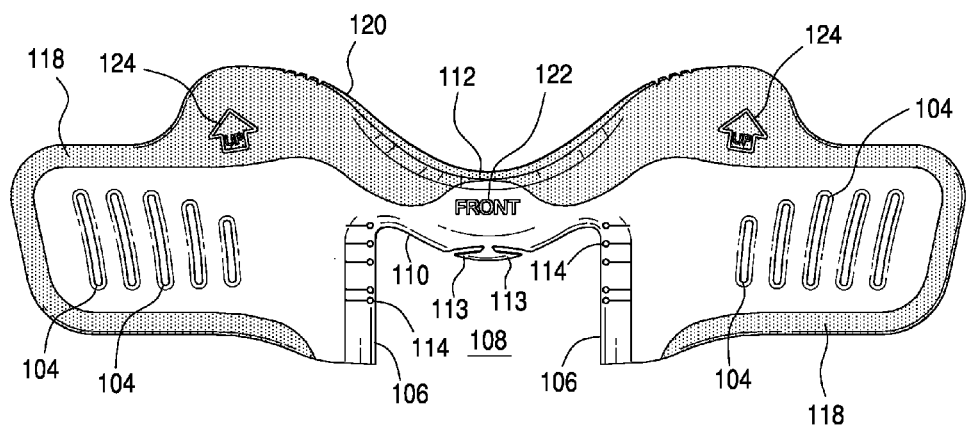
FIG. 2 is a front view of the anterior portion of the cervical collar shown in FIG. 1 with the height adjustment piece removed for the sake of clarity.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary configurations of a cervical collar having height and circumferential adjustment and the respective components thereof, and in no way limit the structures or configurations of a cervical collar and components thereof according to the present disclosure.

DETAILED DESCRIPTION

A. Environment and Context

Embodiments of an orthopedic device are provided for use in stabilizing and supporting anatomical portions of a patient, for example, the neck and head of a patient.

Although the embodiments of the disclosure are adapted for supporting and stabilizing anatomical portions of a large number of patients having various anatomical shapes and sizes, the embodiments of the disclosure may also be dimensioned to accommodate different types, shapes and sizes of anatomical portions.

Exemplary materials and configurations for components of the orthopedic device, such as the structural supports or shells and flexible or compliant portions, as well as exemplary uses and connection mechanisms are described in detail in U.S. Pat. Nos. 5,180,361, granted January 1993, 5,445,602, granted August 1995, 5,622,529, granted April 1997, 5,632,722, granted May 1997, 5,716,335, granted February 1998, 6,071,255, granted June 2000, 6,254,560, granted July 2001, 6,663,581, granted December 2003, 7,018,351, granted March 2006, and 7,198,610, granted April 2007, and all incorporated herein in the entirety by reference.

For ease of understanding the disclosed embodiments of an orthopedic device, the anterior and posterior portions of the orthopedic device are described independently. It will be recognized that the anterior and posterior portions of the orthopedic device function together to form a supporting and stabilizing collar that encompasses the anatomical portions of the wearer.

For further ease of understanding the embodiments of an orthopedic device as disclosed herein, a description of a few terms is necessary. As used herein, the term "proximal" has its ordinary meaning and refers to a location situated next to or near the point of attachment or origin or a central point, or located toward the center of the body. Likewise, the term "distal" has its ordinary meaning and refers to a location that is situated away from the point of attachment or origin or a central point, or located away from the center of the body. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," "compliant," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "compliant" is used to qualify such flexible features as generally conforming to the shape of another object when placed in contact therewith, via any suitable natural or applied forces, such as gravitational forces, or forces applied by external mechanisms, for example, strap mechanisms. The term "resilient" is used to qualify such flexible features as generally returning to an initial general shape without permanent deformation. As for the term "semi-rigid," this term is used to connote properties of support members or shells that provide support and are free-standing, however such support members or shells may have some degree of flexibility or resiliency.

B. Detailed Description of an Anterior Portion of an Orthopedic Device

An anterior portion 100 of an orthopedic device, such as a cervical collar, is shown in FIGS. 1-4. The anterior portion 100 generally includes three components.

The first component is a main support piece 102. The main support piece 102 has the form of a rigid or semi-rigid shell that is formed slightly out of plane to extend towards first and second sides. The main support piece 102 includes a plurality of spaced substantially vertically oriented or angled arcuate slots 104 that aid with ventilation of the orthopedic device in use, and also provide additional resiliency to allow the main support piece 102 to be bent to conform to the anatomical portion of the user, such as the neck.

The main support piece 102 also includes two spaced depending projections 106 that define an open access area 108 therebetween to allow access to, for example, the trachea of a wearer.

A thickened support section 110 runs along the main support piece 102 from a first end of a first depending projection 106 in a generally U-shape along the main support piece 102 to a first end of a second depending projection 106. The thickened support section 110 provides additional support for the main support piece 102 and for the adjustable height support 130 discussed in detail below. As an alternative, a rod or stay that is flexible, such as an aluminum rod, can be integrated into the main support piece 102 in place of the thickened support section 110.

In addition to the thickened support section 110, a supporting spring portion 112 is formed, for example, to support the chin of patient. The supporting spring portion 112 provides a stable but dampening support under the chin of the patient, and restricts flexion. The use of the supporting spring portion 112 in combination with a flexible edge (discussed in more detail below) also aids with reducing or eliminating pressure points.

Ribs 113 are formed below the spring 112 to provide connection points for an attachment piece (chin strut) used to connect a chest plate (forming part of a thoracic extension) to the cervical collar. An exemplary thoracic extension is described in detail in U.S. Pat. No. 6,921,376, granted Jul. 26, 2005, and herein incorporated in the entirety by reference.

Height adjustment indicia 114 are provided on the depending projections to provide easy sizing of the cervical collar using predetermined sizes, such as small, medium, large, etc. The height adjustment indicia 114 can be in the form of standardized, color coded markings and/or lines that reflect standardized marking systems used to indicate patient sizes. Other indicia, such as alphanumeric labels, can also be used. The height adjustment indicia 114 cooperate with leading edges of the adjustable height support 130 to provide an indication of the current sizing of the cervical collar.

Figure 4:
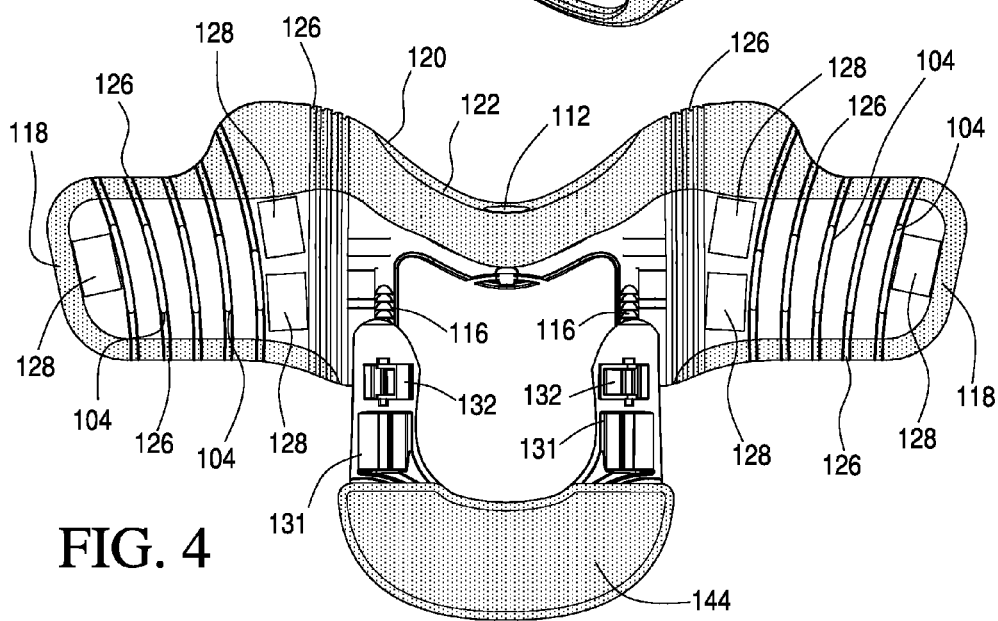
FIG. 4 is a rear view of the anterior portion of the cervical collar shown in FIG. 1.

As seen in FIG. 4, a plurality of locking projections, or ratchets, 116 are formed along each of the depending projections 106 in a linear fashion to cooperate with the adjustable height support 130 discussed in detail below. The locking projections 116 can have a rounded first edge having a first thickness that tapers out to a linear edged having a second thickness that is larger than the first thickness, wherein the linear edge is configured to engage with associated teeth 136 positioned on the adjustable height support 130, as discussed below.

As also shown in FIG. 4, the posterior side of the main support piece 102 includes liner connection points 128, where a suitable removable liner, such as a disposable hydrophilic foam pad liner, can be connected to the cervical collar. The connection points 128 can be formed as hook members, integrally formed on the main support piece 102, for example, by injection molding, and configured to cooperate with loops formed on the liner or attached to the liner. Alternative connection mechanisms, such as hook and loop fasteners applied by adhesive or snap fasteners, can also be used. The use of the integrally formed hooks for the connection points 128 eliminates sharp or rough edges associated with the use of plastic rivets to connect a liner to an orthopedic device, thus providing a more comfortable fit with a reduced chance of pressure sores developing.

The main support piece 102 includes resilient or flexible edges 118 formed along the periphery of the main support piece 102, for example, by overmolding a resilient or compliant material thereon. The use of flexible edges 118 allows the cervical collar to distribute pressure peaks over larger areas in order to avoid the formation of pressure ulcers. The flexible edges 118 can also prevent pressure peaks even when the collar is improperly applied.

The flexible edges 118 can be integrally formed with the second component of the anterior portion 100 of the orthopedic device, a three-dimensional (3D) anatomically configured proximal support portion 120. The 3D anatomically configured proximal support portion 120 can also be formed as a resilient or flexible overmolded portion. The 3D anatomically configured proximal support portion 120 includes an anatomical, generally cup-shaped portion 122 configured to support, for example, the chin of a wearer.

Figure 3:
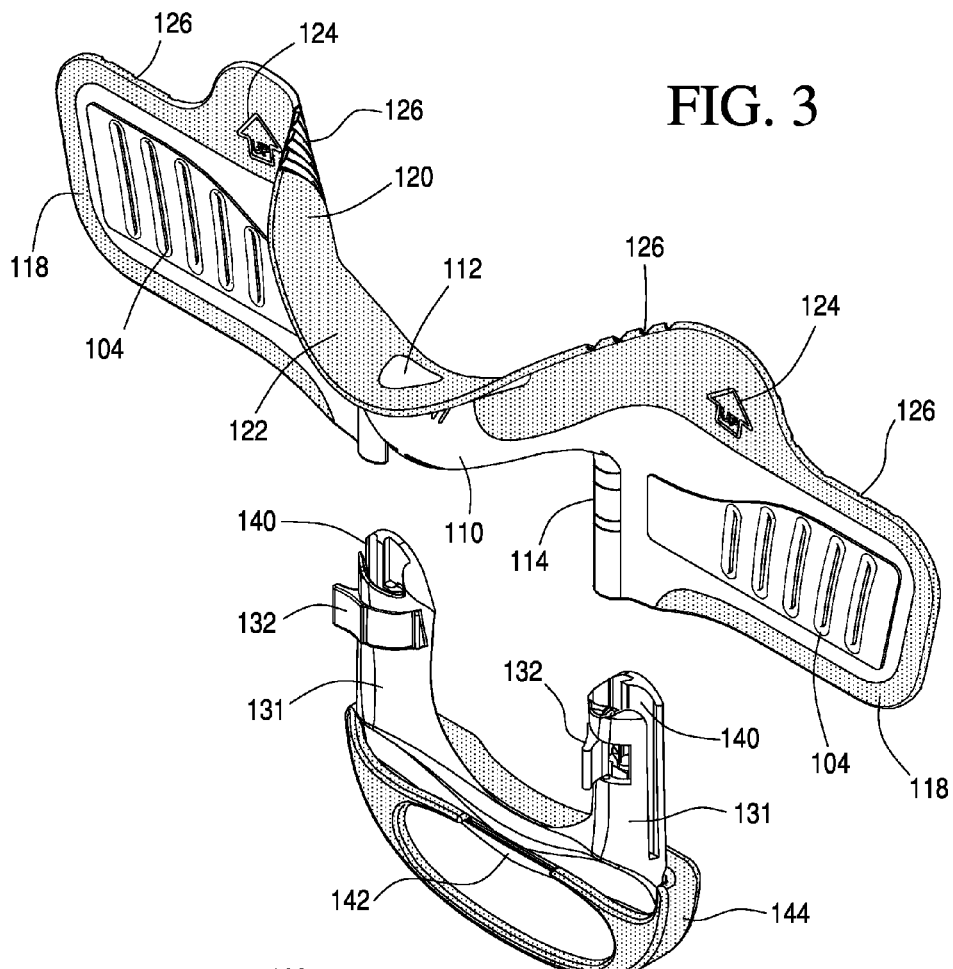
FIG. 3 is a perspective view of the anterior portion of the cervical collar shown in FIG. 1 with the height adjustment piece separated therefrom for the sake of clarity.

As best seen in FIGS. 3 and 4, the 3D anatomically configured proximal support portion 120 is formed around and encompasses the supporting spring portion 112.

Orienting indicia 124, such as arrows and/or words indicating the directions that the anterior main support piece 102 is to be applied to the wearer, can be formed directly in the 3D anatomically configured proximal support portion 120 and also on the main support piece 102. It will be recognized that orienting indicia 124 may take any suitable shape or form and can be positioned on any of the components of the orthopedic device.

As best seen in FIG. 4, fold lines 126 are formed in each of the main support piece 102, the flexible edges 118, and the 3D anatomically configured proximal support portion 120. The fold lines 126 may be created, for example, via a living hinge, which is a reduced thickness portion. Alternatively, the fold lines 126 may be formed by providing a resilient or compliant interface, such as by overmolding, between the portions that are to be folded over. As shown, the fold lines 126 positioned closer to the center line of the anterior portion 100 may be substantially straight, to allow for a sharp fold, while the fold lines 126 positioned closer to the edges of the anterior portion 100 may be arcuate shaped, to allow for more gradual folds. The fold lines 126 allow the anterior portion 100 to be bent or folded to accommodate different circumferences of anatomical portions.

The height of the anterior portion 100 of the orthopedic device can be adjusted to an appropriate size via the use of the third component of the anterior portion 100 of the orthopedic device, the adjustable height support 130. The adjustable height support 130 is configured to be removable from the anterior portion 100, such that the cervical collar can be removed from a patient without removing life support devices that may be connected to the patient in the trachea region, such as breathing and/or feeding tubes. For example, adjustable height support 130 can be removed from the anterior portion 100 of the orthopedic device in order to perform cleaning around or other maintenance of the breathing and/or feeding tubes, while the rest of the orthopedic device remains in place on the patient, or is also removed. Once maintenance is complete, the orthopedic device can be repositioned on the patient and/or the adjustable height support 130 can be reconnected to the orthopedic device.

As best seen in FIG. 3, the adjustable height support 130 includes two upright leg portions 131 configured to cooperate with the depending projections 106. Recessed portions 140 are formed in the upright leg portions 131 and have a corresponding shape to the depending projections 106 for receiving the respective depending projections 106 therein to allow the adjustable height support 130 to be positioned at different heights along the depending projections 106.

As best shown in FIGS. 1, 3, and 4, each upright leg portion 131 includes a locking button 132 that can be manipulated to selectively lock the adjustable height support 130 from being adjusted to a shorter height. The locking buttons 132 are received in appropriately sized and shaped cut out portions of the upright leg portions 131.

Figures 5, 6:
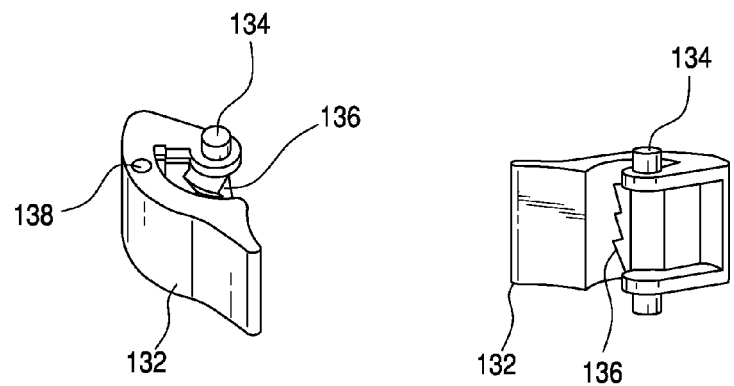
FIGS. 5 and 6 are respectively a side perspective and rear perspective view of the locking button of the height adjustment piece of the cervical collar shown in FIG. 1.

As seen in FIGS. 5 and 6, each locking button 132 includes a pivot axle 134, which is received in the upright leg portion 131, to allow the locking button 132 to be pivoted thereon from an engaged, locked position, to a disengaged, unlocked position. At least one locking protrusion 138 is formed on each locking button 132. The locking protrusion 138 is configured to selectively engage a corresponding portion of the cut out portions of the upright leg portions 131 to selectively lock the locking button 132 in the engaged, locked position in order to prevent accidental movement of the adjustable height support 130 to a shorter height.

Teeth 136 are formed along a reduced thickness portion of the pivot axle 134 for selective engagement with the locking projections or ratchets 116 formed on the depending projections 106. The teeth 136 are formed similarly, but in opposition to, the locking projections or ratchets 116, such that the teeth 136 include a first edge having a first thickness that tapers out to a linear edged having a second thickness that is larger than the first thickness, wherein the linear edges of the teeth 136 engage with the linear edges of the locking projections or ratchets 116 to selectively lock the adjustable height support 130 from being adjusted to a shorter height.

When the locking buttons 132 are pivoted to the disengaged, unlocked position, the teeth 136 are removed from contacting the locking projections or ratchets 116 formed on the depending projections 106. Thus, the adjustable height support 130 can freely move either up or down to either decrease or increase the height. In this manner, the position of the adjustable height support 130 on the associated depending projections 106 can be altered to accommodate different anatomical sizes of wearers.

When the locking buttons 132 are pivoted to the engaged, locked position, the teeth 136 are in contact with the locking projections or ratchets 116 formed on the depending projections 106, and the engagement of the linear edges of the teeth 136 and the locking projections or ratchets 116 prevents the movement of the adjustable height support 130 in the upward direction in order to prevent the adjustable height support 130 from being adjusted to a shorter height. However, since the teeth 136 are formed on a reduced thickness portion of the pivot axle 134, the adjustable height support 130 can be moved downward to be adjusted to an increased height, since the reduced thickness portion of the pivot axle 134 provides resiliency to the teeth 136 and allows the tapered portions of the teeth 136 to slide over the tapered portions of the locking projections or ratchets 116.

In this manner, the position of the adjustable height support 130 on the associated depending projections 106 can be adjusted to increase the height without manipulating the locking buttons 132. This feature is a benefit for quickly applying the cervical collar to a patient. The cervical collar can be packaged with the adjustable height support 130 positioned in the shortest height configuration, in order to save on packaging space, and the locking buttons 132 positioned in the engaged, locked position. The cervical collar can be taken directly from the packaging, and the position of the adjustable height support 130 can be increased to accommodate different sized anatomies, simply by pulling downward on the adjustable height support 130.

Fine tuning of the height of the cervical collar can be achieved by pivoting the locking buttons 132 to the disengaged, unlocked position, and adjusting the height of the adjustable height support 130 as needed.

In a variation, the adjustable height support 130 can be replaced with a support that is still removable, but which is not height adjustable. In particular, the support may still have the locking buttons 132, which may engage one set of projections or ratchets 116 formed on the depending projections 106, which projections or ratchets 116 define a single size setting. In this manner, a collar having a specific set height can be provided, while still allowing the collar to be removed from a patient without removing life support.

As shown in FIGS. 1, 3, and 4 the adjustable height support 130 includes a flared distal end that is configured to engage an anatomical portion, such as the sternum, to provide stabilization and support of the main support piece 102 and the 3D anatomically configured proximal support portion 120 with respect to the respective anatomical portions supported thereby, for example, the neck, chin, and jaw.

A hinged distal connecting portion 142 is connected to the distal end of the adjustable height support 130, and includes a footpad 144 thereon. The hinge of the distal connecting portion 142 can be formed as a living hinge, and allows the distal end of the adjustable height support 130 to pivot to accommodate different sizes and shapes of anatomical portions of patients, for example, the sternum. The footpad 144 can be an integrally formed footpad, or a removable and/or replaceable footpad configured to engage an anatomical portion, such as the sternum. To provide comfort to the wearer and to avoid skin ulceration, the footpad 144 can be a resilient or compliant pad formed, for example, by overmolding. The footpad 144 can also be formed as open or closed cell foam padding, and/or, for example, a disposable hydrophilic foam pad.

The anterior portion 100 of the orthopedic device is configured to cooperate with a posterior portion 146 of the orthopedic device to stabilize and support an anatomical portion of a user, as discussed in detail below.

C. Detailed Description of a Posterior Portion of an Orthopedic Device

Figure 7:
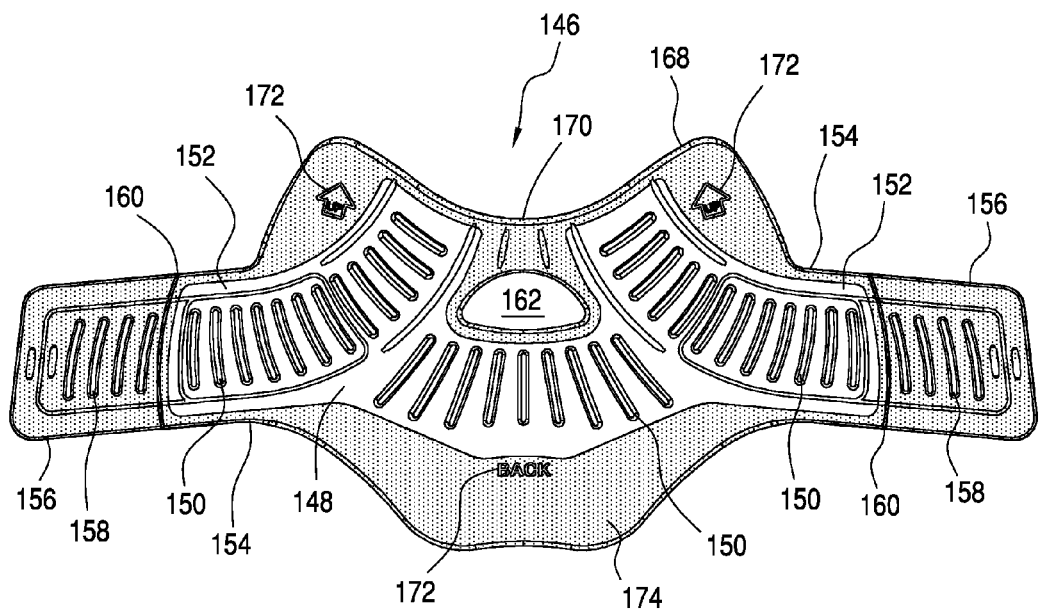
FIG. 7 is a front view of a posterior portion of a cervical collar in accordance with the present disclosure.
Figure 8:
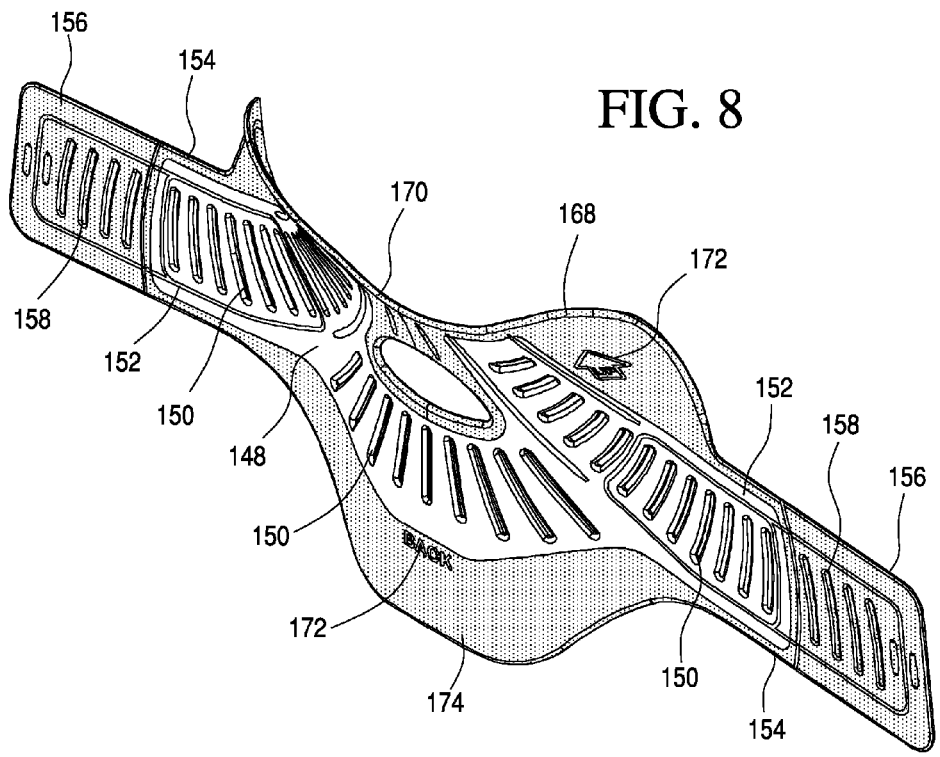
FIG. 8 is a perspective view of the posterior portion of the cervical collar shown in FIG. 7.
Figure 9:
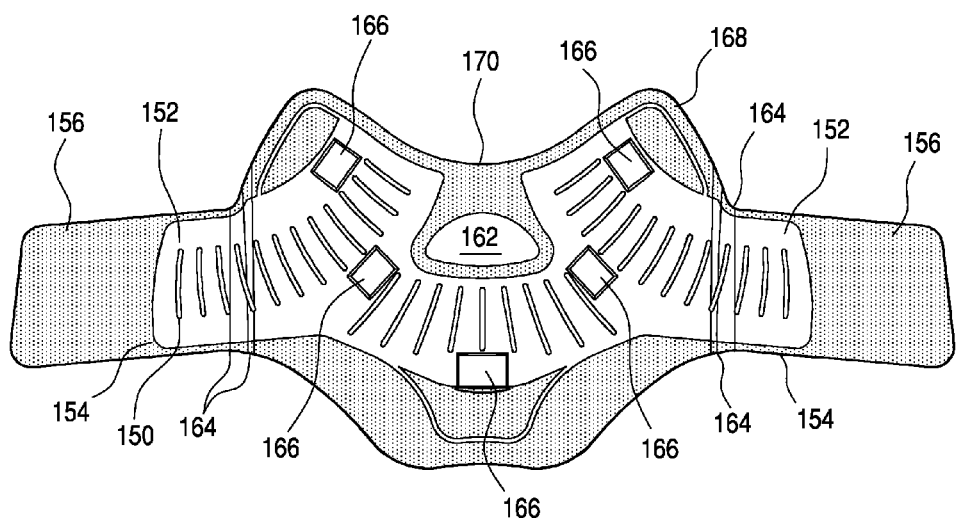
FIG. 9 is a rear view of the posterior portion of the cervical collar shown in FIG. 7.

A posterior portion 146 of an orthopedic device is shown in FIGS. 7-9. The posterior portion 146 of the orthopedic device is constructed in a similar manner as discussed above with respect to the anterior portion, and includes a main support piece 148 and anatomically configured 3D proximal and distal support portions 168, 174.

In a similar manner as previously discussed, the posterior main support piece 148 includes slots 150 that provide ventilation and compliance to the main support piece 148. The slots 150 are formed in three sections of the main support piece 148, the middle section and two upper side sections. The slots 150 in the middle section progress from substantially straight shapes near the center line to slightly arcuate shapes near the edges. The slots 150 in the upper side sections are generally arcuate shapes. The shapes of the slots 150 are specifically configured to provide compliance to the main support piece 148 to allow the posterior portion 146 to conform to different sized anatomical portions of patients. An open cervical access area, 162 is positioned above the middle section and between the upper side sections to provide access to the spine. Further, the main support piece 148 is configured to provide a clearance of the device for the C7 vertebrae.

As with the previously described anterior main support piece, flexible or resilient edges 154 are provided around the periphery of the main support piece 146. The flexible or resilient edges 154 are increased in size from a small flexible edge along the side extending portions 152 that is substantially smaller than the side extending portions 152 to an anatomically configured 3D proximal and distal support portions 168, 174 that may be contiguously formed with the flexible or resilient edges 154 in the proximal and distal central sections. The anatomically configured 3D proximal and distal support portions 168, 174 are of a similar size to the middle section and two upper side sections of the main support piece 148. In this manner, the larger size anatomically configured 3D proximal and distal support portions 168, 174 are able to conform to a large variety of different sizes and shapes of anatomical portions of different users. The flexible or resilient edges 154 and the anatomically configured 3D proximal and distal support portions 168, 174 can be formed, for example, by overmolding.

As best seen in FIG. 8, the proximal support portion 168 includes an anatomically shaped flared section 170 that is shaped to correspond to and support an anatomical portion of a wearer, for example, the occipital region.

As with the anterior portion described above, as shown in FIGS. 8 and 9, orienting indicia 172 are provided on the anatomically configured 3D proximal and distal support portions 168, 174 to indicate the appropriate positioning of the posterior portion 146 of the orthopedic device on the patient. The indicia 172 can be graphically symbolic, and/or alphanumeric in nature, and can be provided in any suitable position on the posterior portion 146.

As best seen in FIG. 9, the anterior surface portion of the posterior portion 146 includes a plurality of liner connection points 166, formed in the same manner and for the same purposes as previously discussed with respect to liner connection points 128. Additionally, fold lines 164, of the same configuration as previously discussed, are also provided to allow the posterior portion 146 of the orthopedic device to be conformed to different sizes and shapes of anatomical portions of patients.

In a slight variation from the anterior portion discussed above, the posterior main support piece 146 includes side extending portions 152 that extend from each side and further include strap portions 156 extending therefrom to aid with circumferential adjustment of the orthopedic device.

The strap portions 156 are formed generally integrally with the flexible or resilient edges 154, and are also flexible or resilient. The strap portions 156 are connected to the side extending portions 152 at trim lines 160, which can be used to more easily remove the strap portions 156 so that the orthopedic device can be used with a proper fit on persons having a very thin anatomical portion, such as a very thin neck.

As can be seen in FIGS. 7 and 8, reduced thickness slots 158 are provided in the strap portions 156. The reduced thickness slots 158 do not pass all the way through the strap portions 156, but still provide additional compliance to allow the strap portions 156 to be more easily bent.

D. Use of Anterior and Posterior Portions Together

Figure 10:
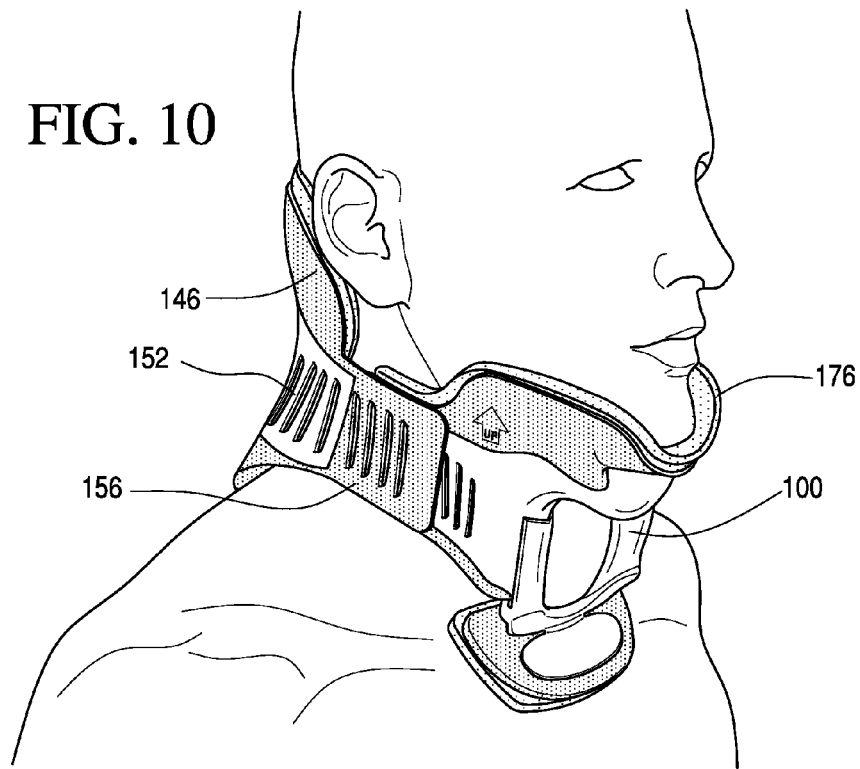
FIGS. 10 and 11 are respectively a front side perspective and rear perspective view of the anterior and posterior portions of the cervical collar together in use on a patient.
Figure 11:
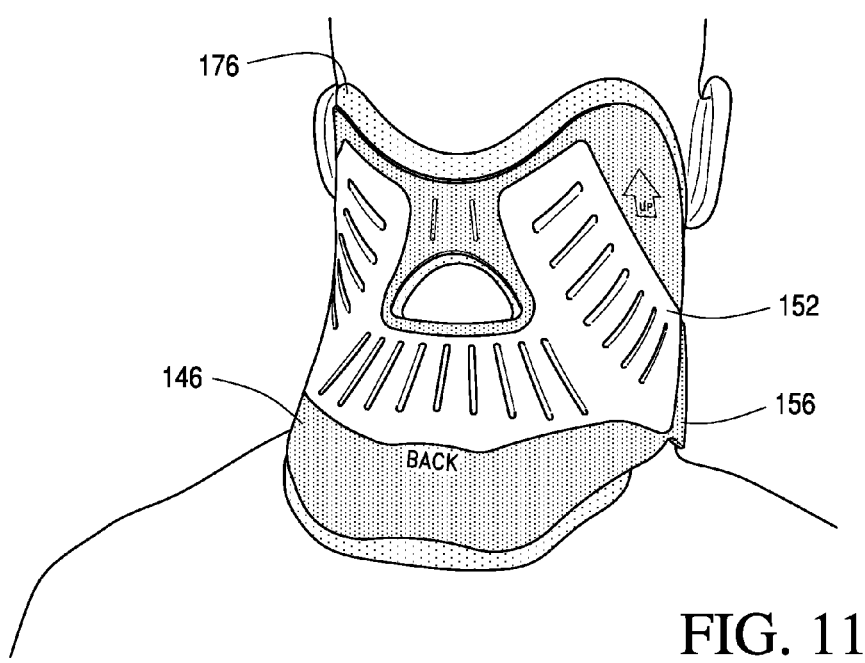

As shown in FIGS. 10 and 11, the anterior and posterior portions 100, 146 are used together to immobilize and stabilize an anatomical portion of a user, such as the neck or cervical area. A two part liner 176 can be provided as an interface between the patient and the respective anterior and posterior portions 100, 146.

As best seen in FIG. 10, the anterior portion 100 is first applied and conformed to the anatomy of the patient. The anterior surface portion of the anterior portion 100 can include integrally formed hooks or loops to form a first part of a hook and loop fastening system. Alternatively, the hooks or loops can be provided as separate pieces that are adhered to the anterior portion 100.

Once the anterior portion 100 is placed on the patient, the posterior portion 146 can be applied. The side extending portions 152 and the strap portions 156 are then folded over the folded portions of the anterior portion 100. Corresponding loops or hooks are similarly integrally formed with or connected to the strap portions 156 (and may be provided on the side extending portions 152 also) for selective engagement with the hooks or loops provided on the anterior portion 100. Since the respective hook and loop fastening elements are provided along a majority of the surfaces of the anterior and posterior portions 100, 146, a wide range of circumferences of anatomical portions of patients can be accommodated.

By way of this strap configuration, there is little to no relative vertical movement between the anterior portion 100 and the posterior portion 146. Thus, the orthopedic device as described herein provides additional immobilization for flexion and extension of the anatomical portion (the neck).

E. Detailed Description of Other Anterior Portions of an Orthopedic Device

Figure 14:
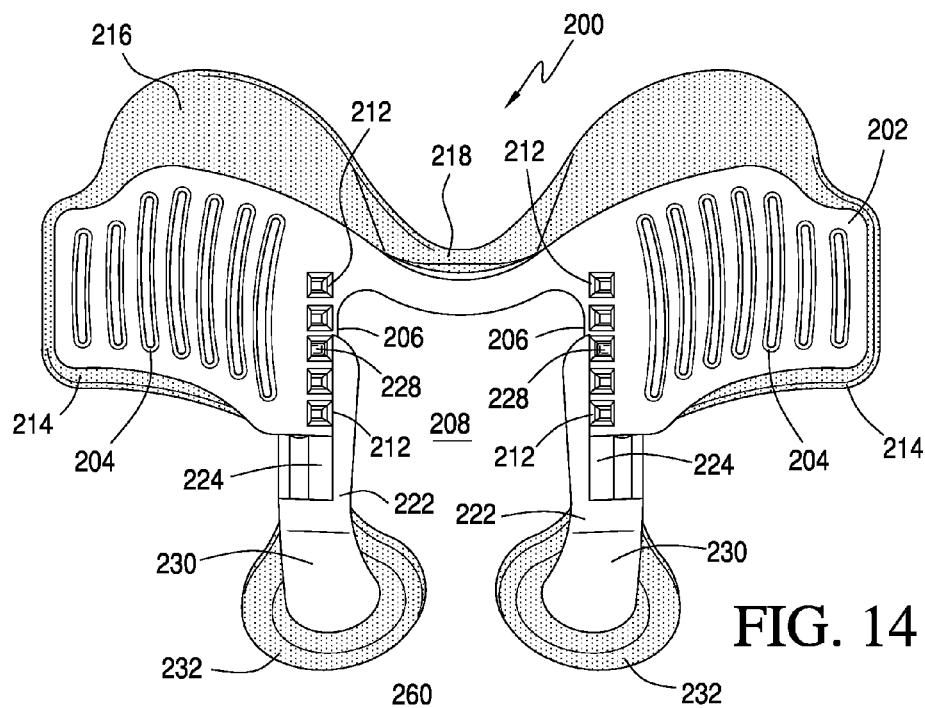
FIG. 14 is a rear view of the anterior portion of the cervical collar shown in FIG. 12.

Another configuration of an anterior portion 200 of an orthopedic device, such as a cervical collar, is shown in FIGS. 12-14. The anterior portion 200 generally includes three components.

The first component is a main support piece 202. The main support piece 202 has the form of a rigid or semi-rigid shell that is formed slightly out of plane to extend towards first and second sides. The main support piece 202 includes a plurality of spaced substantially vertically oriented or angled arcuate slots 204 that aid with ventilation of the orthopedic device in use, and also provide additional resiliency to allow the main support piece 202 to be bent to conform to the anatomical portion of the user, such as the neck.

The main support piece 202 also includes two spaced depending projections 206 that define an open access area 208 therebetween to allow access to, for example, the trachea of a wearer.

A thickened support section 210 runs along the main support piece 202 from a first end of a first depending projection 206 in a generally U-shape along the main support piece 202 to a first end of a second depending projection 206. The thickened support section 210 provides additional support for the main support piece 202 and for the adjustable height supports 222 discussed in detail below. As an alternative, a rod or stay that is flexible, such as an aluminum rod, can be integrated into the main support piece 202 in place of the thickened support section 210.

As seen in FIGS. 12-14, a plurality of locking recesses 212 are formed along each of the depending projections 206 in a linear fashion to cooperate with the adjustable height supports 222 discussed in detail below. The locking recesses 212 can have a substantially rectangular shape with thinned out snap portions along each inner side to snap engage with an associated locking projection 228 positioned on the adjustable height supports 222, as discussed below.

The main support piece 202 includes resilient or flexible edges 214 formed along the periphery of the main support piece 202, for example, by overmolding a resilient or compliant material thereon.

The flexible edges 214 can be integrally formed with the second component of the anterior portion 200 of the orthopedic device, a three-dimensional (3D) anatomically configured proximal support portion 216. The 3D anatomically configured proximal support portion 216 can also be formed as a resilient or flexible overmolded portion. The 3D anatomically configured proximal support portion 216 includes an anatomical, generally cup-shaped portion 218 configured to support, for example, the chin of a wearer.

Orienting indicia 220, such as arrows and/or words indicating the directions that the anterior main support piece 202 is to be applied to the wearer, can be formed directly in the 3D anatomically configured proximal support portion 216. It will be recognized that orienting indicia 220 may take any suitable shape or form and can be positioned on any of the components of the orthopedic device.

The height of the anterior portion 200 of the orthopedic device can be adjusted to an appropriate size via the use of the third component of the anterior portion 200 of the orthopedic device, the adjustable height supports 222.

As best seen in FIGS. 12 and 14, the adjustable height supports 222 include recessed portions 224 that are configured to receive the respective depending projections 206 therein to allow the adjustable height supports 222 to be positioned at different heights along the depending projections 206.

As shown in FIGS. 12-14, each adjustable height support 222 includes a tab 226 formed in the adjustable height support 222. The tab 226 is resiliently biased via cutout lines to allow a locking projection 228 formed on the tab 226 to be selectively positioned within a desired locking recess 212 formed in the associated depending projection 206. In this manner, the position of the adjustable height supports 222 on the associated depending projections 206 can be altered to accommodate different anatomical sizes of wearers.

As best shown in FIG. 12, each adjustable height support 222 includes a flared distal end that is configured to engage an anatomical portion, such as the sternum, to provide stabilization and support of the main support piece 202 and the 3D anatomically configured proximal support portion 216 with respect to the respective anatomical portions supported thereby, for example, the neck, chin, and jaw.

As seen in FIGS. 12-14, each adjustable height support 222 also includes a footpad 232 formed thereon to engage an anatomical portion, such as the sternum. To provide comfort to the wearer and to avoid skin ulceration, the footpads 232 can be resilient or compliant pads formed, for example, by overmolding. The footpads 232 can also be formed as open or closed cell foam padding, or any suitable padding material.

The use of two independent adjustable height supports 222 and the open access area 208 allows the anterior portion 200 of the orthopedic device to be removed from the patient for inspection, cleaning, and/or treatment of the supported anatomical portion, without the need to remove any tubes, such as I.V. or airway/oxygen tubes from the patient.

Figure 15:
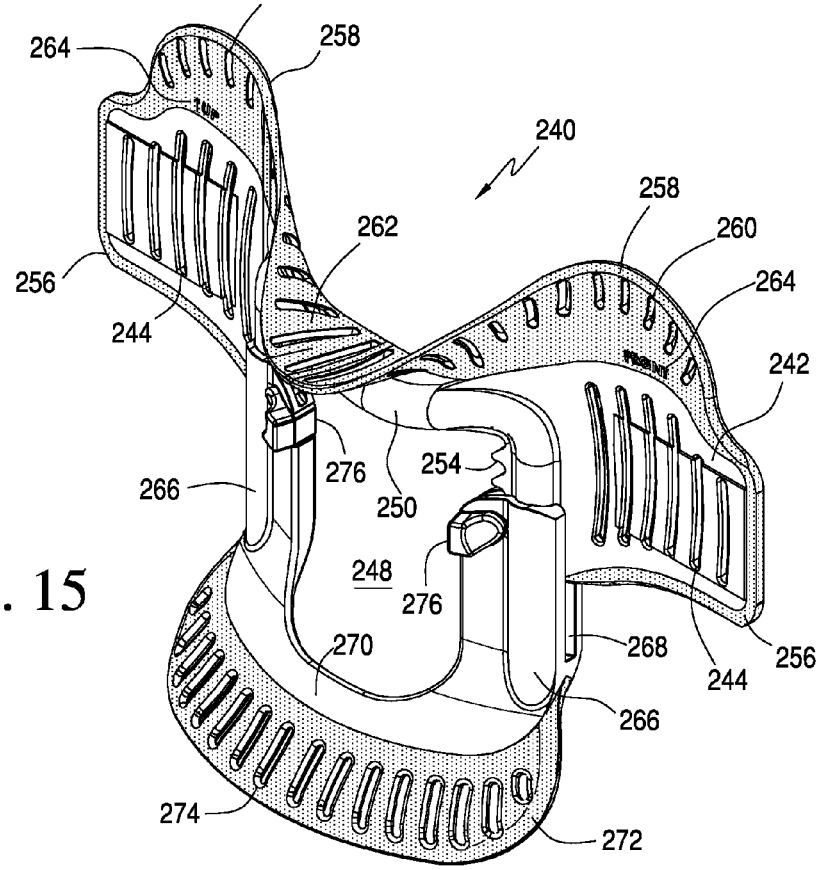
FIG. 15 is a perspective view of another configuration of an anterior portion of a cervical collar in accordance with the present disclosure.
Figure 16:
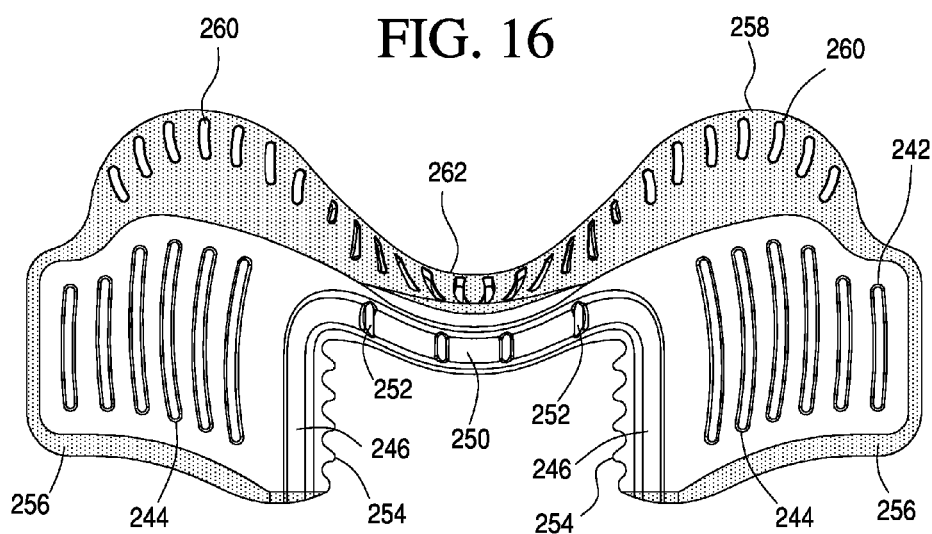
FIG. 16 is a rear view of the main collar piece of the anterior portion of the cervical collar shown in FIG. 15.
Figure 17:
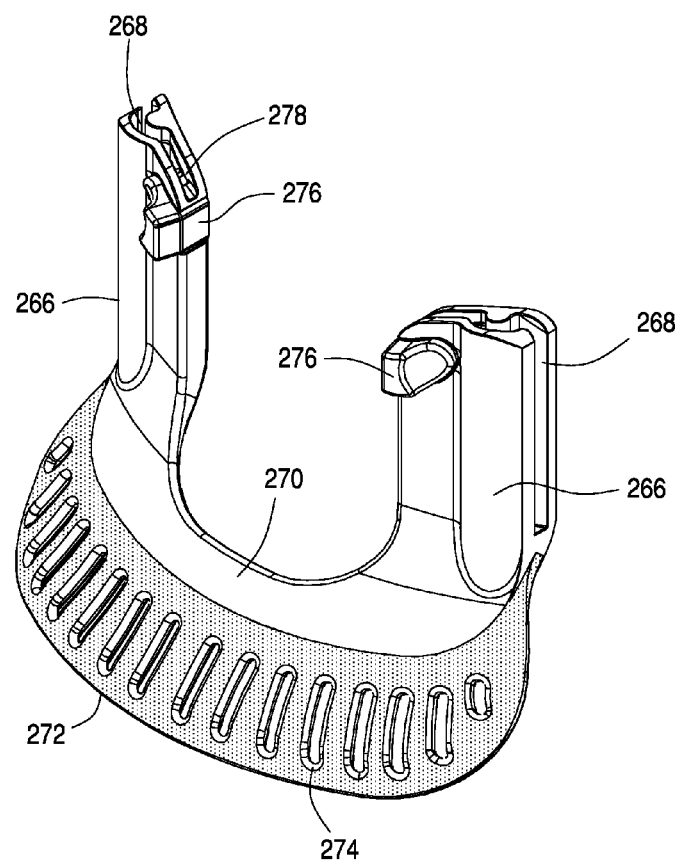
FIG. 17 is a perspective view of the height adjustment piece of the anterior portion of the cervical collar shown in FIG. 15.

A variation of an anterior portion 240 of an orthopedic device, such as a cervical collar, is shown in FIGS. 15-17. The anterior portion 240 is constructed in a similar manner and with similar components as the anterior portion 200 discussed above.

Similarly as described above, the anterior portion 240 includes a main support piece 242 having a plurality of spaced substantially vertically oriented or angled arcuate slots 244 that aid with ventilation of the orthopedic device in use, and also provide additional resiliency to allow the main support piece 242 to be bent to conform to the anatomical portion of the user, such as the neck.

The main support piece 242 also includes two spaced depending projections 246 that define an open access area 248 therebetween to allow access to, for example, the trachea of a wearer. Similarly as discussed above, a thickened support section 250 runs along the main support piece 242 in a generally U-shape along the depending projections 246 and the main support piece 242 to provide additional support for the main support piece 242 and for the adjustable height supports 266 discussed in detail below.

As seen in FIG. 16, the thickened support section 250 includes cut outs 252 on the posterior side of the main support piece 242 to provide additional resiliency or flexibility to the main support piece 242.

As best seen in FIG. 16, a series of locking projections or ratchets 254 are formed along the sides of the depending projections 246 in a linear fashion to cooperate with the adjustable height supports 266 discussed in detail below.

Like the previously described configuration, the main support piece 242 includes resilient or flexible edges 256 formed along the periphery of the main support piece 242, for example, by overmolding a resilient or compliant material thereon.

The flexible edges 256 can be integrally formed with a three-dimensional (3D) anatomically configured proximal support portion 258. The 3D anatomically configured proximal support portion 258 can also be formed as a resilient or flexible overmolded portion. The 3D anatomically configured proximal support portion 258 includes slots 260 formed therein to promote ventilation and resilience or compliance, and an anatomical, generally cup-shaped portion 262 configured to support, for example, the chin of a wearer.

As above, orienting indicia 264 can be formed directly in the 3D anatomically configured proximal support portion 258 or on other components of the anterior portion 240 of the orthopedic device.

Like the previous configuration, the height of the anterior portion 240 of the orthopedic device can be adjusted to an appropriate size via the use of the adjustable height supports 266.

Unlike the previous configuration, and as best seen in FIGS. 6 and 17, the adjustable height supports 266 are connected together at their distal ends by a flared distal connecting portion 270. A footpad 272 is attached to the flared distal connecting portion 270, for example by overmolding. The footpad 272 includes slots 274 to aid with ventilation and resiliency or flexibility of the footpad 272.

As best seen in FIG. 17, each of the adjustable height supports 266 includes a recessed portion 268 that is configured to receive a respective depending projection 246. The depending projections 246 have a curved shape for the thickened support section 250, which shape is complementary to the shape of the recessed portions 268 shown in FIG. 17.

In order to provide selective height adjustment, each adjustable height support 266 includes a tab 276 formed in the adjustable height support 266. The tab 276 is resiliently biased via cutout lines to allow a locking projection or pawl 278 formed integrally with the tab 276 to be selectively positioned along the locking projections or ratchets 254. In this manner, the position of the adjustable height supports 266 on the associated depending projections 246 can be altered to accommodate different anatomical sizes of wearers.

F. Components of an Orthopedic Device

A variation of an anatomically configured 3D proximal support portion 280 for use with an anterior portion of an orthopedic device is shown in FIG. 18.

The proximal support portion 280 is formed in substantially the same manner as the main support pieces 202, 242 described above, having slots 282 therein and flexible or resilient edges 284 formed, for example, as overmolded edges.

The proximal support portion 280 can be attached to a main support piece at specified locations via recessed rivets 286, which are best seen in FIG. 19.

As shown in FIGS. 20 and 21, the proximal support portion 280 has 3D anatomically configured portions 288, 290 that are shaped corresponding to anatomical portions of the wearer, for example the jaw line and the chin.

In a further variation of 3D proximal support portion 280, as shown in FIG. 22, a cushion or pad 292 is formed along the central portion thereof to provide a comfortable fit for the wearer and to prevent skin ulcerations. The pad 292 may be a compliant or resilient overmolded pad or may be an open or closed cell foam pad.

Figure 27:
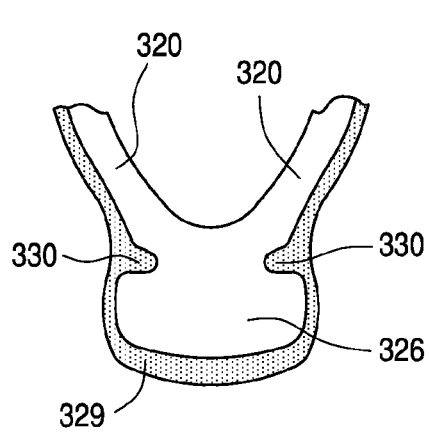
FIGS. 27 and 28 are front views of various alternate configurations of sternum footpads in accordance with the present disclosure.

A variation of another component for use with an orthopedic device is shown in FIG. 27. In particular, a modified adjustable height support section 300 is shown in FIG. 27. The adjustable height support section 300 has a similar function and configuration as the adjustable height support sections previously discussed. Accordingly, the adjustable height support section 300 has a flared distal connection portion 302 extending between the upright portions. The flared distal connection portion 302 includes a flexible or compliant edge 304 formed along the distal portion thereof. The edge can be formed, for example, by overmolding. The flexible or compliant edge 304 includes slots to provide ventilation and/or compliance.

In addition to the above structure, the adjustable height support section 300 also includes a removable and/or interchangeable footpad 308. The footpad 308 can be a compliant or resilient overmolded pad or a compliant or resilient open or closed cell foam pad made from any suitable material. Different footpads 308 may be provided having different characteristics, for example, different stiffnesses or different thicknesses. The footpad 308 may be removed to allow for some reduction in support and stability to allow a user more range of motion while still providing sufficient restriction to prevent further injury. Such additional range of motion may be useful during activities, such as eating, where the wearer needs additional range of motion, but does not want to remove the entire orthopedic device to obtain the additional range of motion.

Figure 23:
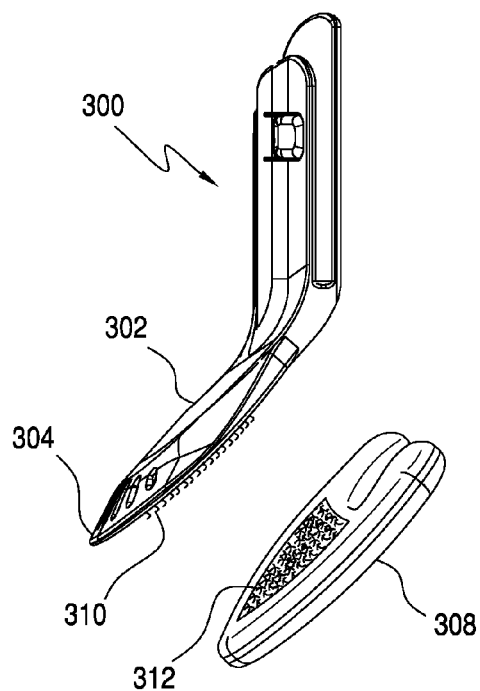
FIG. 23 is a side view of a variation of an adjustable height support in accordance with the present disclosure with a removable and/or interchangeable pad detached.

As shown in FIG. 23, the footpad 308 is removably attached to the flared distal connecting portion 302 and the flexible or compliant edge 304. The footpad 308 can be connected using hook and loop material 310, 312 secured to or integrally formed with the respective components. Alternative fastening mechanisms, such as snap fasteners, can also be used.

As shown in FIG. 23, the hook material 310 is carried by the flared distal connecting portion 302 and the flexible or compliant edge 304 and the loop material 312 is carried by the footpad 308. It will be recognized that the placement of the hook and loop material 310, 312 can be alternated.

Other various configurations of footpads or shims suitable for use with any of the disclosed portions of an orthopedic device are shown in FIGS. 24-30.

Figure 24:
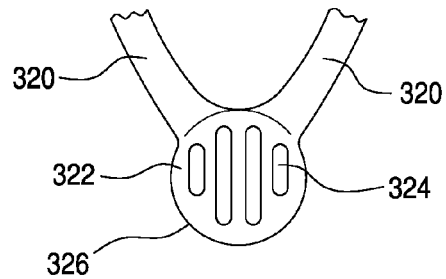
FIG. 24 is a front view of an alternate configuration of a sternum footpad in accordance with the present disclosure.
Figure 28:
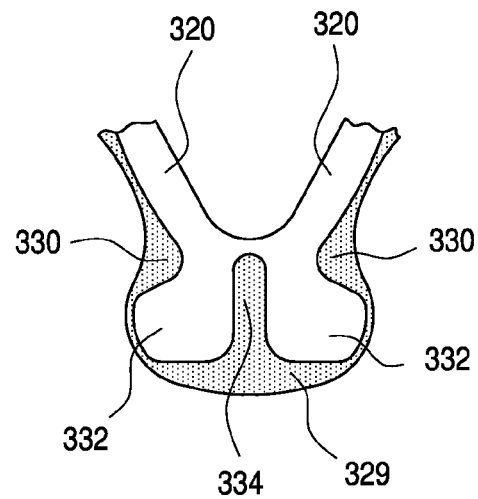

As shown generally in FIGS. 24, 27, and 28, supporting struts 320 depend and converge at a distal support piece 322. The distal support piece 322 may include slots 324 and other various geometrical configurations to provide comfort to a user.

Figure 25:
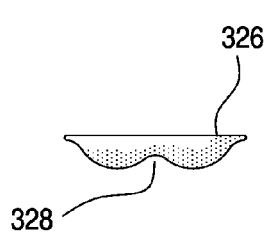
FIG. 25 is a bottom view of the sternum footpad shown in FIG. 24.

For example, as shown in FIG. 25, a compliant or resilient footpad 326, formed, for example, by overmolding, includes a pressure relief channel 328 formed therein.

Other configurations utilizing compliant or resilient edges 329, formed, for example, by overmolding around a footpad 326 are shown in FIGS. 27 and 28. The footpads 326 of these configurations, and as shown in FIG. 28, can include various geometrical configurations including side recesses 330, side flanges 332, and/or a central recess 334 to aid with allowing the footpad 326 to adjust to the different anatomical contours of different users.

Figure 29:
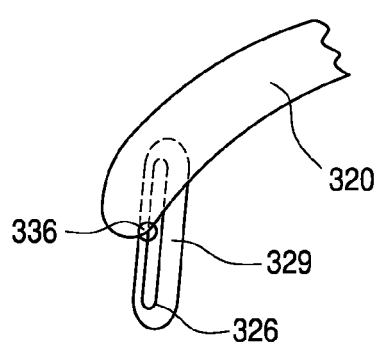
FIG. 29 is a side view of an alternate configuration of a sternum footpad in accordance with the present disclosure.
Figure 30:
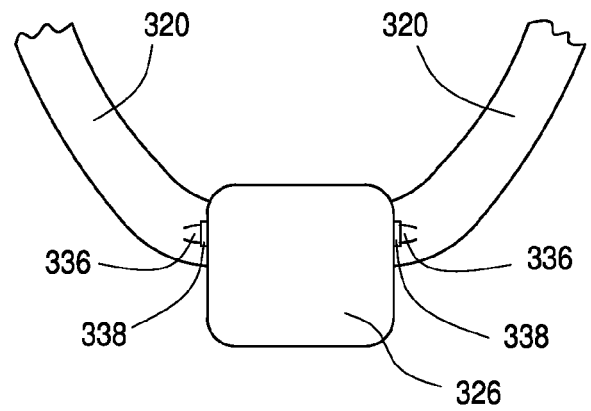
FIG. 30 is a rear view of the sternum footpad shown in FIG. 29.

In a further variation designed to allow the footpad 326 to adjust to patient shape, and as shown in FIGS. 29 and 30, the footpad 326 is connected to the supporting struts 320 via pivot points or pins 136 and pivot connections 338. This configuration allows the footpad 326 to pivot or rotate about the supporting struts 320 to accommodate various different sizes and shapes of wearers. Footpads having different properties can be interchangeably positioned via the pivot connections.

Figure 26:
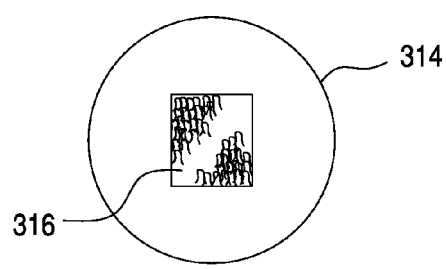
FIG. 26 is a front view of a shim member for use with a cervical collar in accordance with the present disclosure.

As shown in FIG. 26, one or more removable and/or interchangeable shims 314 can be used to provide small adjustments in height and/or range of motion of the orthopedic device. The exemplary shim 314 can be a thin piece of material, such as plastic, or open or closed cell foam. Shims 314 can be added, removed, and stacked beneath any of the discussed footpads to provide fine adjustments in height and/or range of motion of the orthopedic device. The shims 314 can have any suitable shape that complements the shape of the footpad or section of the orthopedic device to which they are attached.

As shown in FIG. 26 each side of the shim 314 includes a connection mechanism 316, such as hook and loop fasteners or snap fasteners. The connection mechanisms 316 are used to removably attach a shim 314 to the orthopedic device and/or another shim 314. The shims 314 can be used to provide fine adjustments in height and/or range of motion of the orthopedic device for activities such as eating to allow the wearer to conduct these activities without having to completely remove the orthopedic device.

G. Detailed Description of Posterior Portions of an Orthopedic Device

Another configuration of a posterior portion 340 of an orthopedic device is shown in FIGS. 31-35.

The posterior portion 340 of the orthopedic device is constructed in a similar manner as discussed above with respect to the anterior portions, and includes a main support piece 342 and an anatomically configured 3D proximal support portion 362. While not specifically shown in this configuration, a height adjustment mechanism can be utilized with the posterior portion 340 of the orthopedic device in a similar manner as discussed above with respect to the anterior portions of the orthopedic device, or as further discussed below.

In a similar manner as previously discussed, the posterior main support piece 342 includes slots 344 and depending projections 346 that define an open access area 348 to provide access to anatomical portions of the wearer, for example cervical or spinal access.

In a slight variation from the anterior portions discussed above, the posterior main support piece 342 includes side extending portions 350 that extend from each side to aid with circumferential adjustment of the orthopedic device, as will be discussed in detail below.

As with previously described anterior main support pieces, flexible or resilient edges 352 are provided around the periphery of the main support piece 342. The flexible or resilient edges 352 can be formed, for example, by overmolding.

Similarly to the anterior main supporting pieces, the posterior main support piece 342 includes an anatomically configured 3D proximal support portion 362 that may be contiguously formed with the flexible or resilient edges 352. The proximal support portion 362 includes slots 364 that aid with ventilation and add flexibility or resiliency thereto.

Figure 31:
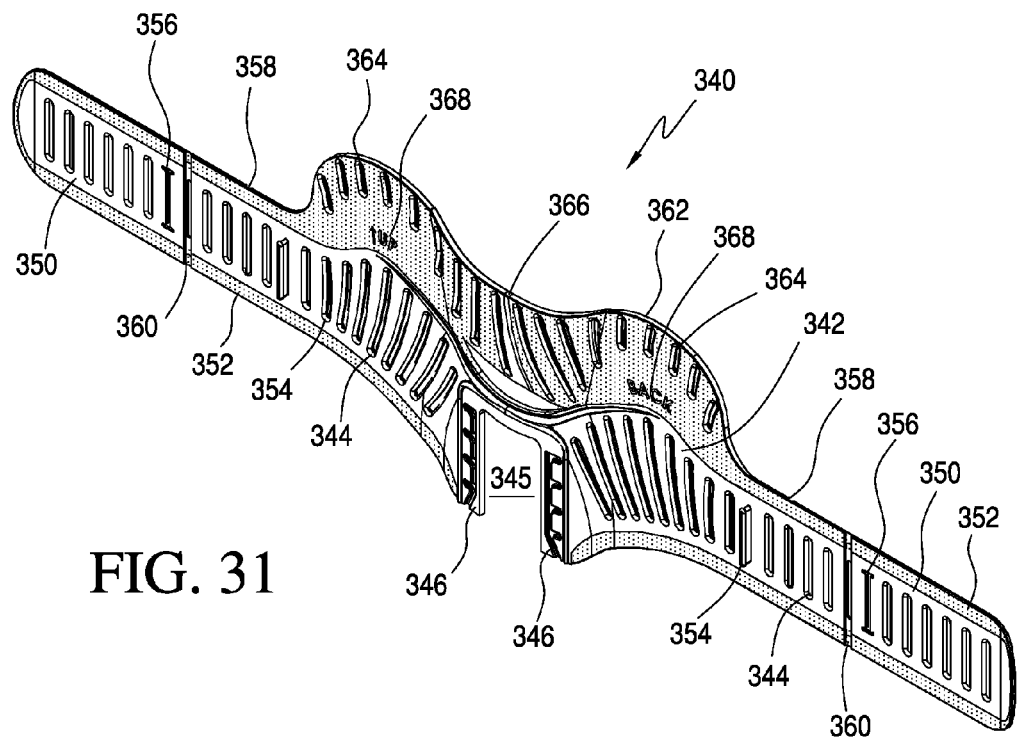
FIG. 31 is a perspective view of another configuration of a posterior portion of a cervical collar in accordance with the present disclosure.
Figure 32:
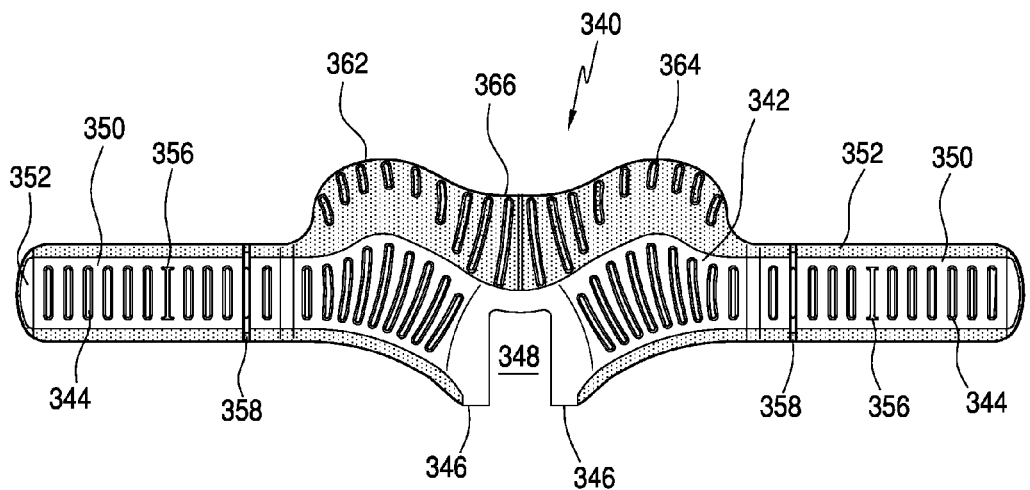
FIG. 32 is a rear view of the posterior portion of the cervical collar shown in FIG. 31.
Figure 33:
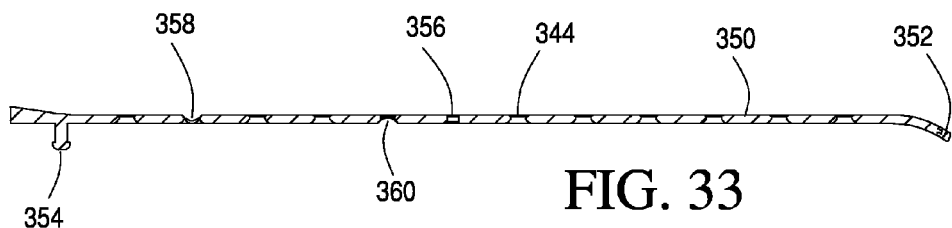
FIG. 33 is a partial sectional view of the side extending portion in FIG. 32.

As best seen in FIG. 31, the proximal support portion 362 includes an anatomically shaped flared section 366 that is shaped to correspond to and support an anatomical portion of a wearer, for example, the occipital region.

As with the anterior proximal support portions described above, as shown in FIG. 31, orienting indicia 368 are provided on the posterior proximal support portion to indicate the appropriate positioning of the posterior portion of the orthopedic device on the patient.

The posterior main support piece 342 also includes a mechanism to allow for circumferential adjustment of the orthopedic device in use on a patient to accommodate different anatomical sizes of patients. The circumferential adjustment also accommodates changes in anatomical size of a single patient due to an increase or decrease of swelling in the treated anatomical portion.

Figure 34:
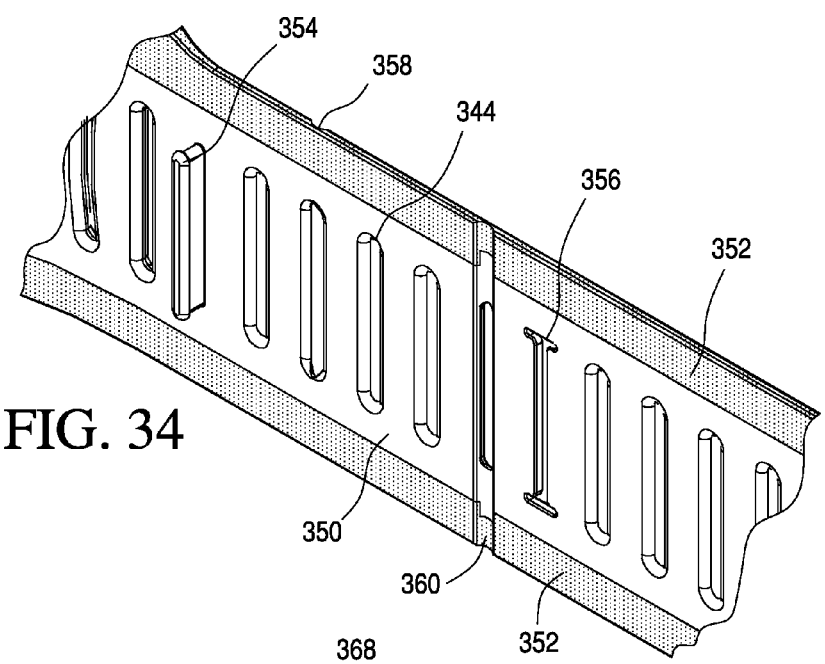
FIG. 34 is a partial expanded view of a portion of the posterior portion of the cervical collar shown in FIG. 31.
Figure 35:
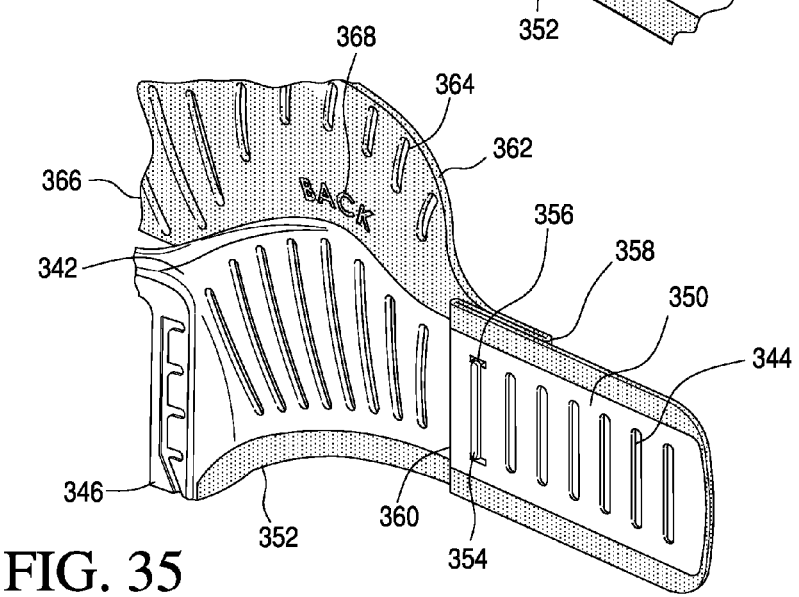
FIG. 35 shows the side extending portion of FIG. 32 folded over to adjust the length of the posterior portion of the cervical collar shown in FIG. 32 to adjust the circumference of the overall cervical collar.
Figure 36:
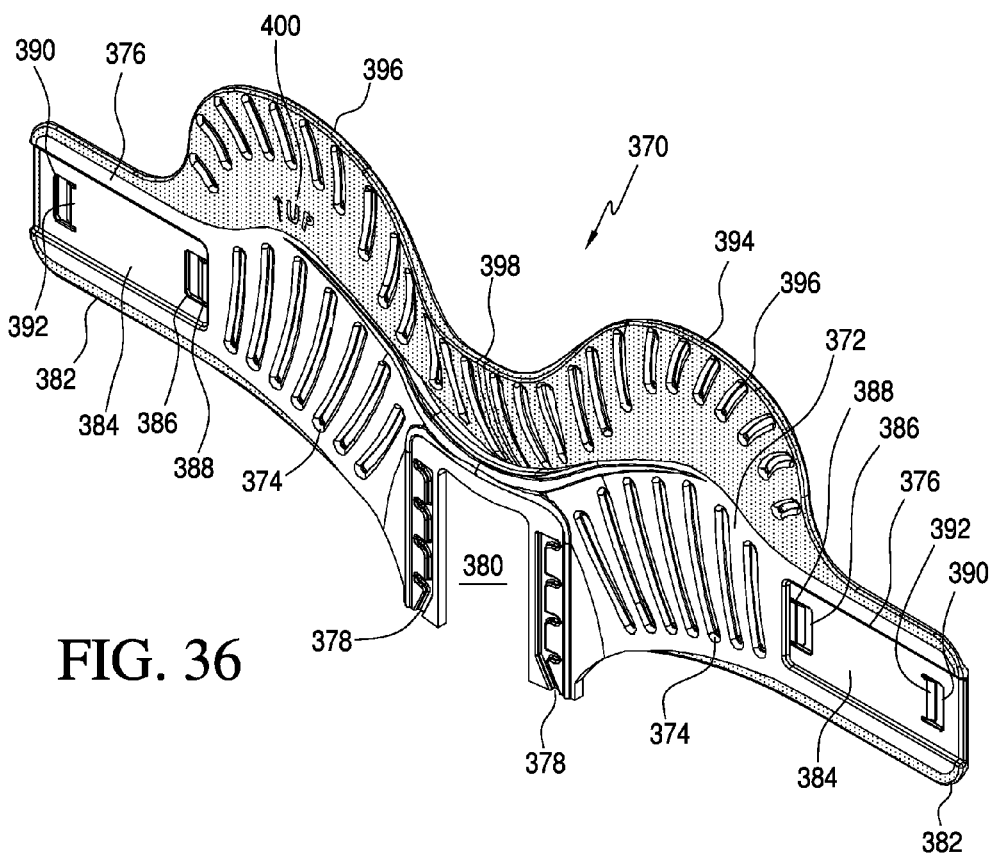
FIG. 36 is a perspective view of another configuration of a posterior portion of a cervical collar in accordance with the present disclosure.
Figure 37:
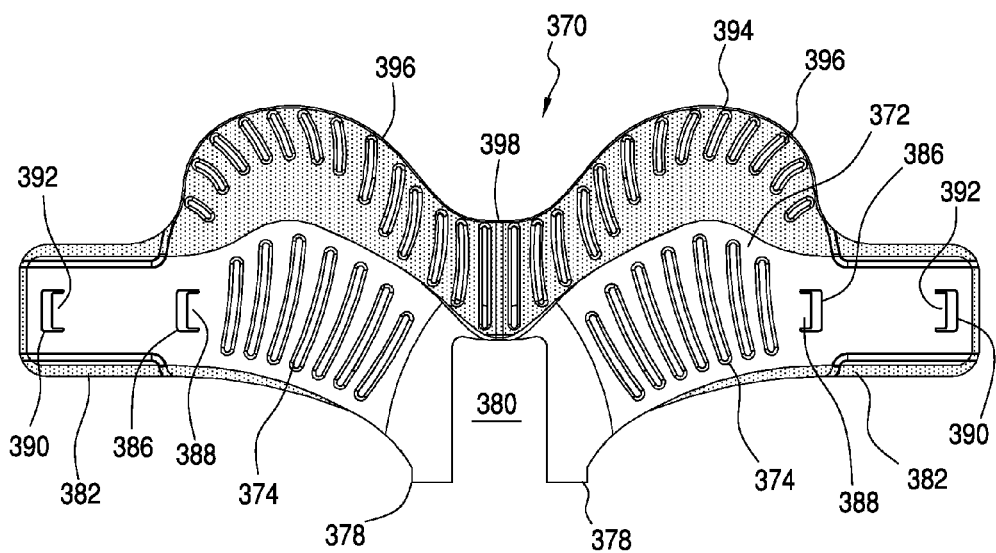
FIG. 37 is a rear view of the posterior portion of the cervical collar shown in FIG. 36.

To provide a circumferential adjustment mechanism, as best seen in FIGS. 31 and 34, a locking projection 354 is positioned on each of the side extending portions 350. A corresponding locking recess 356 is positioned in a portion of the each side extending portions 350 at a point spaced from the respective locking recess 356. It will be recognized that the positions of the locking projection 354 and the respective locking recess 356 can be alternated from the shown configuration. The locking projection 354 and the respective locking recess 356 can be formed in a snap locking configuration.

In order to adjust the circumference of the orthopedic device, the side extending portions 350 can be folded over to reduce their respective lengths. First and second fold lines 358, 360 are positioned between the spaced locking projection 354 and locking recess 356 to allow the side extending portions 350 to be folded about to bring the locking projection 354 and locking recess 356 into engagement to selectively lock the respective side extending portion 350 into a shortened configuration.

The first and second fold lines 358, 360 may be created, for example, via a living hinge, which is a reduced thickness portion. Alternatively, the first and second fold lines 358, 360 may be formed by providing a resilient or compliant interface, such as by overmolding, between the portions of the side extending portions 350 that are to be folded over.

In the configuration shown in FIG. 31 with the side extending portions 350 fully extended, the orthopedic device can accommodate larger or swollen anatomical portions. In the folded configuration shown in FIG. 35, the orthopedic device can now accommodate smaller anatomical portions, or anatomical portions that have decreased in size via a reduction in swelling.

Another configuration of a posterior portion 370 of an orthopedic device is shown in FIGS. 36-41.

The posterior portion 370 of the orthopedic device is constructed in a manner similar to the posterior portion 340 and includes a main support piece 372 and an anatomically configured 3D proximal support portion 394.

The main support piece 372 includes slots 374 formed therein and side extending portions 376. Spaced depending projections 378 define an open access area 380 therebetween to allow access to an anatomical portion of a wearer, for example the cervical or spinal area. The main support piece 372 also includes resilient or compliant edges 382 formed thereon, for example, via overmolding.

The anatomically configured 3D proximal support portion 394 can be contiguously formed with the resilient or compliant edges 382. The proximal support portion 394 includes slots 396 formed therein to provide ventilation and/or additional resilience or flexibility. The proximal support portion 394 also includes an anatomically shaped flared section 398 that is shaped to correspond to and support an anatomical portion of a wearer, for example, the occipital region. As with previous configurations, orienting indicia 400 is formed on the proximal support portion 394 to aid with applying the orthopedic device to a patient.

Like the previously discussed posterior portion 340, the posterior portion 370 also includes a mechanism to provide for circumferential adjustment of the orthopedic device.

In particular, as shown in FIGS. 36 and 38-41, the side extending portions 376 each include a recessed receiving portion 384 for receiving a side connection piece 402 therein. Positioned within each recessed receiving portion 384 are first and second locking recesses 386, 390 and associated first and second biasing members 388, 392. The two corresponding locking recess and biasing member combinations allow the side connection pieces 402 to be positioned at two locations along the side extending portions 376. It will be recognized that additional locking recess and biasing member combinations can be provided to allow for additional positioning of the side connection pieces 402 along the side extending portions 376.

As shown in FIGS. 38 and 39, each side connection piece 402 has first and second sides 404, 406 and a flared end 408 configured for gripping by a user. The first side 404 of the side connection piece 402 has a manipulation tab 410 configured for manipulation by a user, along with the flared end 408, for attaching and removing the side connection piece 402 from the recessed receiving portion 484 and repositioning the side connection piece 402 therein.

The second side 406 of the side connection piece 402 has a locking projection 412 formed thereon for selectively engaging one of the locking recess and biasing member combinations 386-392 formed in the recessed receiving portion 384.

As best seen in FIGS. 39-41, the locking projection 412 can be in the form of a snap locking projection that is biased into a locked position in the recesses 386, 390 via the biasing members 388, 392. When the side connection piece 402 is selectively engaged with the second locking recess 390, the orthopedic device can accommodate larger or swollen anatomical portions. When the side connection piece 402 is selectively engaged with the first locking recess 386, the orthopedic device can now accommodate smaller anatomical portions, or anatomical portions that have decreased in size via a reduction in swelling. In this manner, the circumference of the orthopedic device can be adjusted.

As shown in FIG. 39, the second side 406 of the side connection piece 402 can also include an area of connection material 414, for example loop material. The connection material 414 is configured to selectively engage connection material, such as hook material, that is position on or formed on the anterior surface of the anterior portion of the orthopedic device to arrange the posterior and anterior portions around an anatomical portion of a wearer to provide support and stabilization thereto. The flared end of the side connection piece aids with connecting the posterior and anterior portions around an anatomical portion of a wearer by providing a suitable gripping or grasping area.

H. Variations of Circumferential Adjustment for an Orthopedic Device

Figure 42:
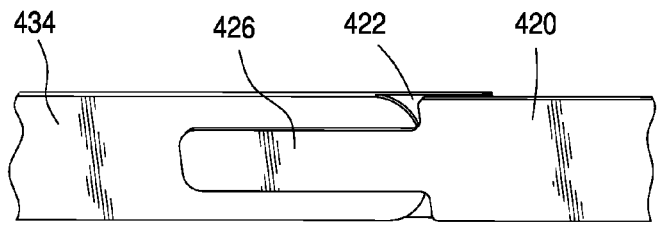
FIGS. 42 and 43 are schematic views of a variation of a circumferential adjustment mechanism for use with cervical collars in accordance with the present disclosure.
Figure 43:
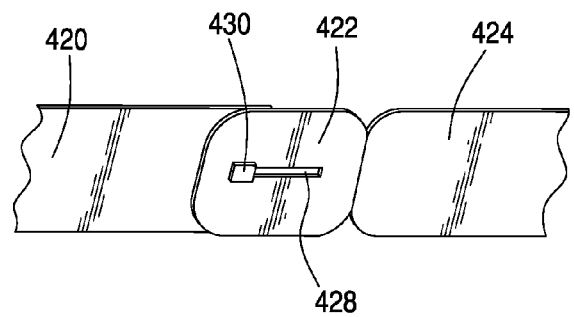
Figure 44:
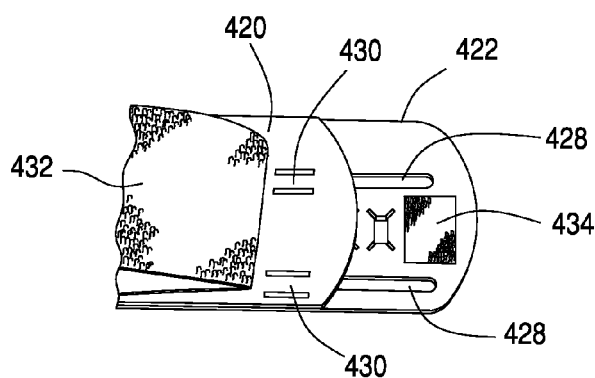
FIG. 44 shows an exemplary configuration of the circumferential adjustment mechanism shown in FIGS. 42 and 43.

A variation of a circumferential adjustment mechanism for an orthopedic device is shown in FIGS. 42-44.

As shown schematically in FIG. 42, a posterior support piece 420 is attached to an anterior support piece 424 via a connection member 426 utilizing, for example, hook and loop fastening. The posterior support piece 420 and anterior support piece 424 can be of any of the disclosed configurations or variations.

Since the hypothetical patient using the orthopedic device as shown in FIG. 42 either has a smaller circumference anatomical portion or has no or reduced swelling, the posterior support piece 420 and anterior support piece 424 contact each other to support the anatomical portion, for example the neck.

As can best be seen in FIG. 43, in the case where the patient has a larger circumference anatomical portion or has increased swelling, a circumferential expansion piece 422 is provided between the posterior support piece 420 and anterior support piece 424 to allow the posterior support piece 420 and anterior support piece 424 to expand with respect to each other to accommodate the larger or swollen anatomical portion.

As best seen in FIG. 43, the circumferential expansion piece 422 includes an expansion slot 428 thereon in which a sliding projection 430 that extends from the posterior support piece 420 slides within. Thus, in order to accommodate larger or swollen anatomical portions, the expansion piece 422 is slid along the expansion slot 428 from the position shown in FIG. 42 to the position shown in FIG. 43. In this manner, the circumferential expansion piece 422 provides additional support between the posterior support piece 420 and anterior support piece 424 when the orthopedic device is applied to larger or swollen anatomical portions.

A working example of this circumferential adjustment system (without the anterior support piece shown) is shown in FIG. 44. As shown in FIG. 44, the posterior support piece 420 carries a connection material 432, for example loop material, that is folded back to show the circumferential expansion piece 422 and expansion slots 428.

The expansion piece 422 carries a second connection material 434, for example hook material, that selectively engages the connection material 432. In this configuration the circumferential size of the orthopedic device can be finely adjusted by sliding the expansion piece 422 along the expansion slots 428 to a desired position. The expansion piece 422 can then be locked into place using the connection materials 432, 434.

Figure 45:
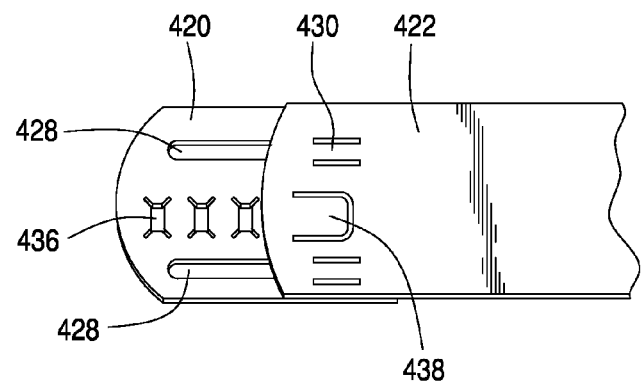
FIG. 45 shows another variation of a circumferential adjustment mechanism for use with cervical collars in accordance with the present disclosure.

In another variation of a circumferential adjustment system, shown in FIG. 45, the connection materials are replaced with a series of locking recesses 436 and two expansion slots 428 positioned on the posterior support piece 420. In this configuration, the expansion piece 422 carries sliding projections 430 to engage the expansion slots 428. The expansion piece 422 also includes a locking projection 438 that is biased via cutouts in a manner previously discussed. The locking projection 438 is thus configured to selectively engage one of the series of locking recesses 438 on the posterior support piece 420.

Thus, the circumferential size of the orthopedic device can be incrementally adjusted to a number of specific sizes to accommodate larger or swollen anatomical portions.

Figure 46:
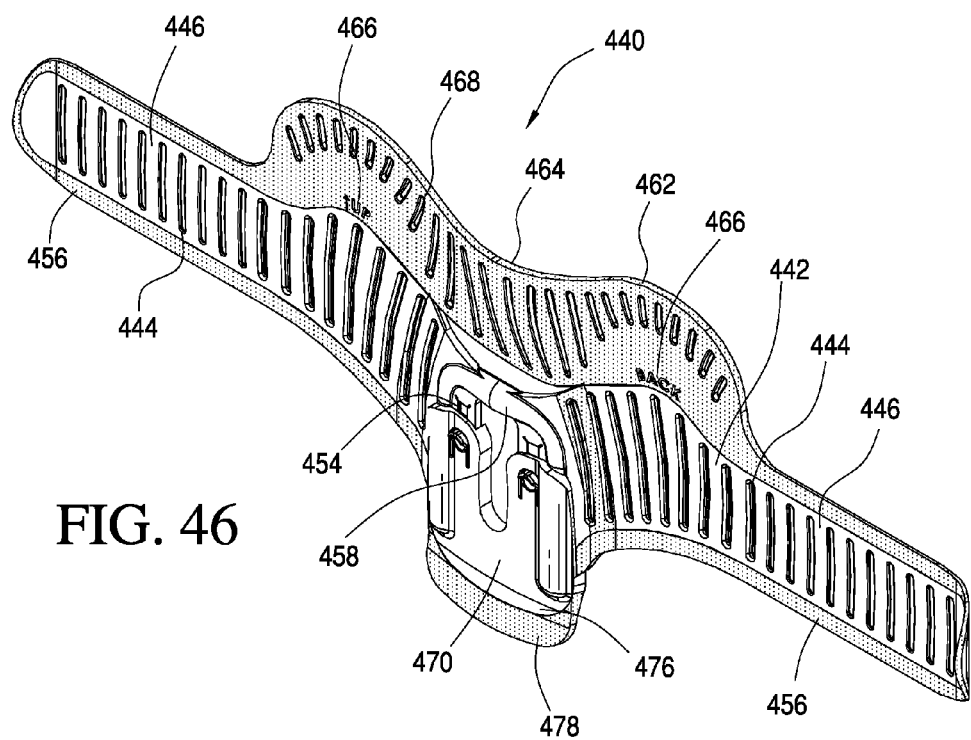
FIG. 46 is a perspective view of another configuration of a posterior portion of a cervical collar in accordance with the present disclosure.
Figure 47:
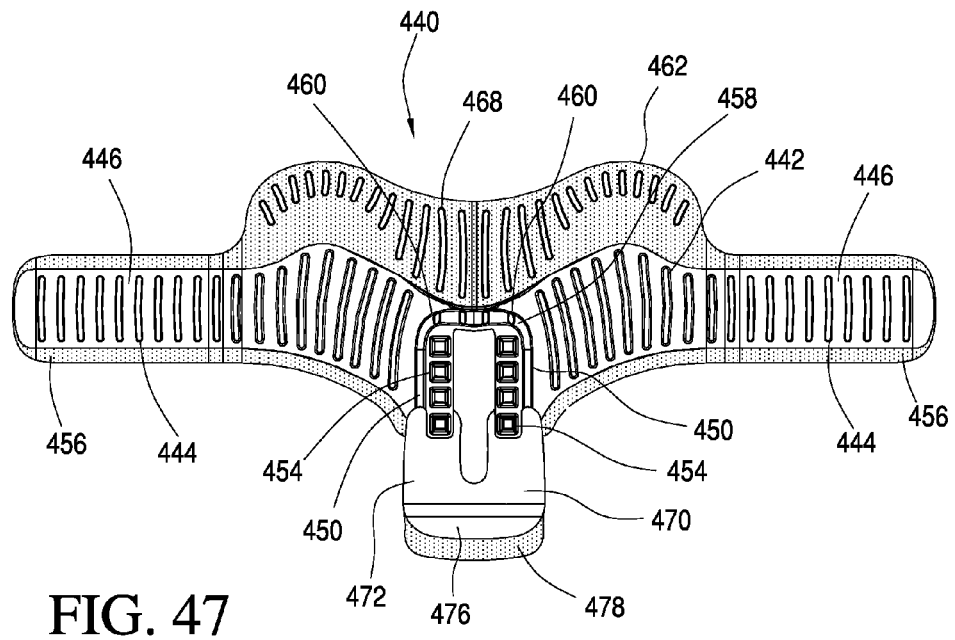
FIG. 47 is a rear view of the posterior portion of the cervical collar shown in FIG. 46.
Figure 48:
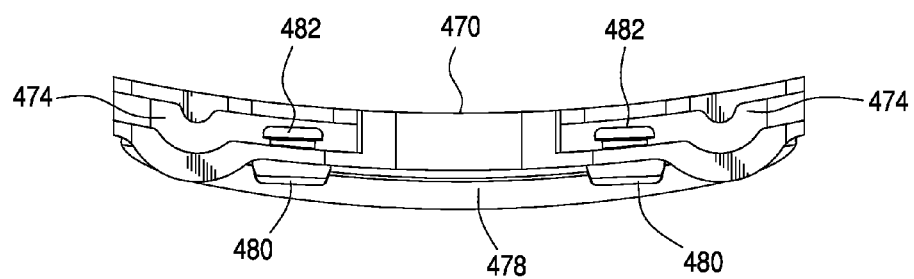
FIG. 48 is a top view of the height adjustment piece of the posterior portion of the cervical collar shown in FIGS. 46 and 47.

I. Detailed Description of a Variation of a Posterior Portion of an Orthopedic Device Another variation of a posterior portion 440 of an orthopedic device is shown in FIGS. 46-48. The posterior portion 440 includes mechanisms for both height and circumferential adjustment, which mechanisms can be utilized with any of the aforementioned anterior or posterior portions for an orthopedic device.

The posterior portion 440 is constructed in a similar manner as discussed above and includes a main support piece 442, a 3D anatomically configured proximal support portion 462, and an adjustable height support 470.

The main support piece 442 includes slots 444 to provide ventilation and flexibility or resilience. Side extending portions 446 extend from the main support piece 442 towards an anterior support portion of the orthopedic device. The side extending portions 446 have reduced thickness sections 448 extending towards the ends thereof.

The reduced thickness sections 448 will have a connection mechanism, such as hook or loop material, that will selectively engage with a corresponding connection material positioned on an anterior support portion of the orthopedic device. The reduced thickness sections 448 allow the side extending portions 446 to be bent around an anterior support portion of the orthopedic device in order to provide a desired circumferential size for the orthopedic device. The enhanced flexibility or resiliency of the reduced thickness sections 448 of the side extending portions 446 allows the side extending portions 446 to be bent in a smaller radius of curvature to accommodate smaller sized anatomical portions.

The main support piece 442 also has spaced depending projections 450 that define an open access area therebetween to allow access to an anatomical portion of a wearer, for example cervical or spinal access. A thickened support section 458 is formed along the main support piece 442 and the depending projections 450. Cutouts 460 in the thickened support section 458 are provided on the anterior side of the main support piece 442 to aid with allowing the main support piece 442 to conform to the shape of the treated anatomical portion.

As shown in FIGS. 46 and 47, a series of locking recesses 454 are formed along each of the depending projections 450 for selectively engaging a locking projection 482, in manner as discussed above with regard to the first configuration of an anterior portion of an orthopedic device.

The main support piece 442 also includes flexible or resilient edges 456, for example, overmolded portions. The 3D anatomically configured proximal support portion 462 can be contiguously formed with the flexible or resilient edges 456.

The 3D anatomically configured proximal support portion 462 has an anatomically shaped flared section 464 that is shaped to correspond to and support an anatomical portion of a wearer, for example, the occipital region. Orienting indicia 466 and slots 468 are also provided on the 3D anatomically configured proximal support portion 462.

As shown in FIGS. 47 and 48, the adjustable height support 470 includes two spaced upright portions 472 that have recessed portions 474 configured to receive the depending projections 450 in a height adjusting manner. The adjustable height support 470 has a flared distal end 476 that has a footpad 478 attached or formed thereon, for example, by overmolding.

A tab 480, biased by cutout portions in a manner previously discussed, is provided on each upright portion 472. A locking projection 482 is formed with the tab 480 to selectively engage a locking recess 454 in the depending projection 450 of the main support piece 440. The adjustable height support 470 can be incrementally positioned at different heights via the selective engagement of the tabs 480 with associated locking recesses 454.

J. Detailed Description of Another Variation of a Posterior Portion of an Orthopedic Device Another variation of a posterior portion 490 of an orthopedic device, which is similar in construction to the posterior portion 440 discussed above, is shown in FIGS. 49 and 50.

The posterior portion 490 includes a main support piece 500, having slots 502 to provide ventilation and/or compliance, side extending portions 504 each having a reduced thickness section 506, and spaced depending projections 508 defining a spinal or cervical access area 510 therebetween and configured to cooperate with any of the previously discussed height adjustment mechanisms. Indicia 512 to indicate appropriate sizing, such as XS (extra small), S (standard/small), M (medium), and L (large), or any other appropriate indications, such as color coded indicia, can be provided in any suitable location on the main support piece 500, for example, on the depending portions 508. A flexible or compliant edge 514 is provided around the periphery of the main support piece 500. The flexible or compliant edge 514 can be formed, for example, via overmolding.

Figure 49:
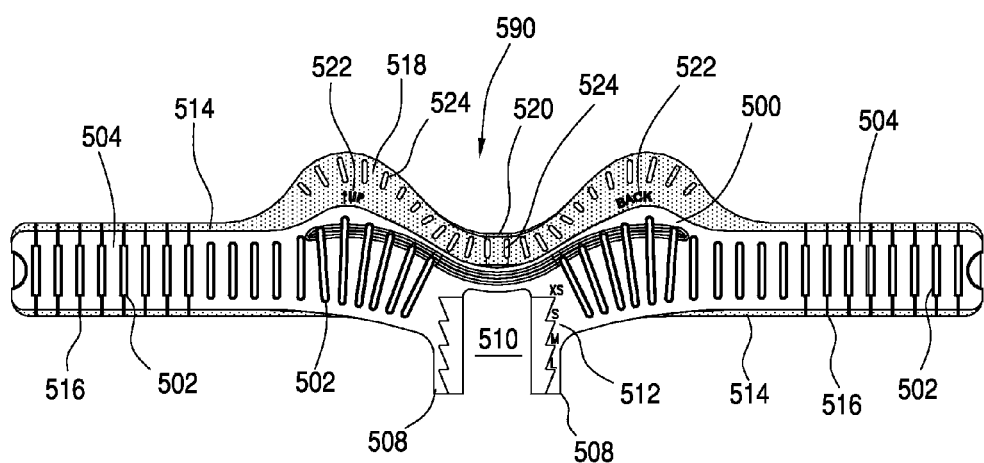
FIG. 49 is a front view of another variation of a posterior portion of a cervical collar according to the present disclosure.
Figure 50:
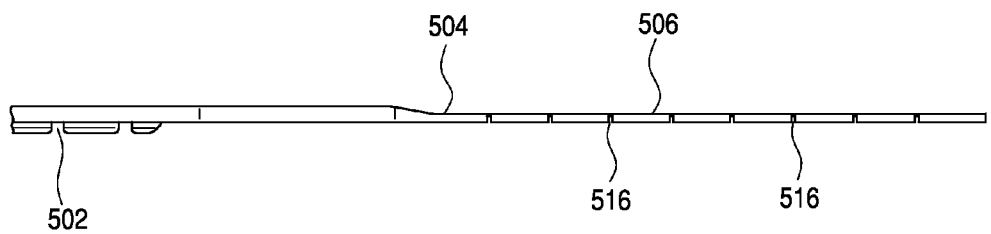
FIG. 50 is an expanded top view of a side extending portion of the posterior portion of the cervical collar shown in FIG. 49.

As best seen in FIGS. 49 and 50, fold lines 516 are formed in the reduced thickness sections 506 of the side extending portions 504. As previously discussed, such fold lines 516 can be formed, for example, as living hinges or as a compliant interface formed, for example by overmolding, between sections of the side extending portions 504. The reduced thickness sections 506 in combination with the fold lines 516 allow the side extending portions 504 to be bent or folded to accommodate different circumferences of anatomical portions.

The posterior portion 490 also includes a proximal support portion 518, which can be a 3D flexible or compliant support having an anatomically shaped flared section 520 that is shaped and configured to support an anatomical portion of a wearer, such as the occipital region of the head. The proximal support portion 518 can be an overmolded portion that is formed integrally with the flexible or compliant edge 514 on the main support piece 500. The proximal support portion 518 can include orienting indicia 522 and slots 524 to provide ventilation and/or compliance.

K. Conclusion

The disclosed embodiments of an orthopedic device, such as a cervical collar, having anterior and posterior portions that are positioned about an anatomical portion of a wearer, such as the neck, to conform thereto and provide support, immobilization, and stabilization thereto, provide many improvements that allow a single orthopedic device to be applied for treatment to a wide variety of patients having varying sizes or degrees of swelling of anatomical portions.

It is understood that while the disclosed embodiments are designed to accommodate users having different sized anatomies, the size of the disclosed embodiments and the components thereof can be adjusted so that different users having different sized anatomical portions may benefit from the present designs.

It is understood that while the disclosed embodiments of the orthopedic device are shown having discrete anterior and posterior portions, the anterior and posterior portions may be connected with each other along one side thereof, and a single strap or circumferential adjustment mechanism can be provided between the anterior and posterior portions along the other side thereof.

It will also be recognized that the overmolded edges and 3D anatomical portions, as well as the living hinge and slot structures, can be provided to a collar, without providing other features, such as the height adjustability, to the collar.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features from different embodiments. In addition to the variations described herein, other known equivalents for each feature can be mixed and matched by one of ordinary skill in this art to construct an orthopedic device in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A cervical collar comprising:
an anterior main support piece having a proximal support portion and a removable height adjustment mechanism lockable at a plurality of locations on the anterior main support piece, wherein the main support piece includes first and second spaced depending projections that are selectively received within corresponding first and second proximally extending upright leg portions on the removable height adjustment mechanism.

2. The cervical collar according to claim 1, further comprising:
a posterior main support piece having a proximal support portion and a circumferential adjustment mechanism including at least a strap portion formed in a side extending portion of the posterior main support piece.

3. The cervical collar according to claim 2, wherein the anterior and posterior main support piece each have flexible or resilient edges formed thereon.

4. The cervical collar according to claim 3, wherein the flexible or resilient edges are overmolded along a periphery of the respective anterior and posterior main support piece.

5. The cervical collar according to claim 3, wherein the anterior and posterior proximal support portions are contiguously formed with the respective resilient edges of the anterior and posterior main support pieces.

6. The cervical collar according to claim 2, wherein the posterior main support piece includes a distal support portion.

7. The cervical collar according to claim 6, wherein the posterior distal support portion is a flexible or resilient, overmolded portion.

8. The cervical collar according to claim 6, wherein the posterior distal support portion is an anatomically configured three-dimensional support portion.

9. The cervical collar according to claim 2, wherein the strap portion is a flexible or resilient, overmolded portion.

10. The cervical collar according to claim 2, wherein the anterior and posterior proximal support portions are anatomically configured three-dimensional support portions.

11. The cervical collar according to claim 2, wherein the anterior and posterior proximal support portions are flexible or resilient, overmolded portions.

12. The cervical collar according to claim 2, wherein the anterior and posterior main support pieces include a plurality of slots formed therein to provide ventilation and resiliency to the anterior and posterior main support pieces.

13. The cervical collar according to claim 2, further comprising indicia formed on at least one of the anterior and posterior main support pieces for orienting the anterior and posterior main support pieces.

14. The cervical collar according to claim 2, further comprising:
   fold lines formed in each of the anterior and posterior main support pieces.

15. The cervical collar according to claim 1, wherein the height adjustment mechanism comprises:
   the first and second upright leg portions formed together with a flared distal end;
   a locking button pivotally connected to each of the first and second upright leg portions for selectively engaging locking projections formed on the first and second depending projections of the anterior main support piece; and
   a footpad on the flared distal end.

16. The cervical collar according to claim 1, further comprising height adjustment indicia provided on the first and second depending projections cooperating with the removable height adjustment mechanism to indicate a current size of the cervical collar.

17. The cervical collar according to claim 1, wherein a thickened support section runs along the anterior main support piece from a first end of the first depending projection to a first end of the second depending projection.

18. The cervical collar according claim to 1, further comprising:
   at least one locking button provided in one of the first and second upright leg portions for selective engagement with locking projections formed on the respective first or second depending projection; and
   wherein when the locking button is in a disengaged, unlocked position, the height adjustment mechanism can be moved in both the proximal and distal directions, and when the locking button is in an engaged, locked position, the height adjustment mechanism can be moved in the distal direction only.

19. A cervical collar comprising:
   an anterior main support piece having a proximal support portion and a removable height adjustment mechanism, wherein the main support piece includes first and second spaced depending projections that are selectively received within corresponding first and second upright leg portions on the removable height adjustment mechanism;
   wherein the anterior main support piece is formed from a main support piece and a flexible edges extending about a substantial portion of the periphery of the main support piece, the flexible edges being more flexible than the main support piece.

20. A cervical collar comprising:
   an anterior main support piece having a proximal support portion and a removable height adjustment mechanism, wherein the main support piece includes first and second spaced depending projections that are selectively received within corresponding first and second upright leg portions on the removable height adjustment mechanism;
   at least one locking button provided in one of the first and second upright leg portions for selective engagement with locking projections formed on the respective first or second depending projection; and
   wherein when the locking button is in a disengaged, unlocked position, the height adjustment mechanism can be moved in both the proximal and distal directions, and when the locking button is in an engaged, locked position, the height adjustment mechanism can be moved in the distal direction only.

* * * * *